(12) United States Patent
Alker et al.

(10) Patent No.: US 6,262,046 B1
(45) Date of Patent: Jul. 17, 2001

(54) AZETIDINYLPROPYLPIPERIDINE DERIVATIVES, INTERMEDIATES AND USE AS TACHYKININ ANTAGONISTS

(75) Inventors: David Alker, Sandwich; Thomas Victor Magee, Mystic; Graham Nigel Maw; Donald Stuart Middleton, both of Sandwich, all of (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/423,771

(22) PCT Filed: Jul. 1, 1998

(86) PCT No.: PCT/EP98/04177

§ 371 Date: Nov. 10, 1999

§ 102(e) Date: Nov. 10, 1999

(87) PCT Pub. No.: WO99/01451

PCT Pub. Date: Jan. 14, 1999

(30) Foreign Application Priority Data

Jul. 4, 1997 (GB) .................................................. 9714129

(51) Int. Cl.[7] .................................................. C07D 267/02
(52) U.S. Cl. .............................. 514/211.15; 514/217.04; 514/219; 514/235.5; 514/252.18; 514/316; 514/326; 540/544; 540/575; 540/597; 544/129; 544/360; 546/187; 546/208
(58) Field of Search .................... 540/544, 575, 540/597; 544/129, 360; 546/187, 208; 514/211.15, 217.04, 219, 252.18, 235.5, 316, 326

(56) References Cited

U.S. PATENT DOCUMENTS

| 5,625,060 | 4/1997 | Emonds-Alt et al. ................ 540/524 |
| 5,656,639 | 8/1997 | Emonds-Alt et al. ................ 514/305 |

FOREIGN PATENT DOCUMENTS

| 0791592 | 8/1997 | (EP) . |
| WO9605193 | 2/1996 | (WO) . |
| 9725322 A1 | 7/1997 | (WO) . |
| WO9725322 * | 7/1997 | (WO) . |
| WO9901451 | 1/1999 | (WO) . |

OTHER PUBLICATIONS

Rupniak, N.M.J. et al, Trends Pharmacol. Sci., 20, 1999, 485–490.*
Bernstein, C.N. et al, Am. J. Gastroenterol., 88, 1993, 908–913, cited in Medline PMID 7684884.*
Stedman's Medicianl Dictionary, Williams & Wilkins, Montvale, NJ, 1995.*
Burne, R.A. et al, Microbes Infect., 2, 2000, 533–542.*
Mobley, H.L.T. et al, Microbiol. Rev., 1989, 85–108.*
Collins, C.M. et al, Mol. Microbiol., 9, 1993, 907–913.*

* cited by examiner

Primary Examiner—Mukund J. Shah
Assistant Examiner—Thomas McKenzie
(74) Attorney, Agent, or Firm—Peter C. Richardson; Gregg C. Benson; A. Dean Olson

(57) ABSTRACT

Compounds of the formula (I):

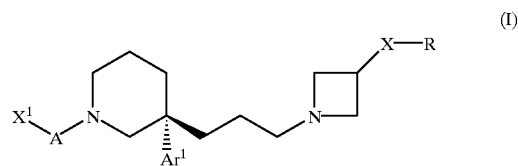

where $X^1$, A, $Ar^1$, X and R are as defined in the specification, and pharmaceutically-acceptable salts thereof, are new, and are useful as tachykinin inhibitors which act at the $NK_1$, $NK_2$ and $NK_3$ receptors or a combination of two or more thereof.

22 Claims, No Drawings

AZETIDINYLPROPYLPIPERIDINE DERIVATIVES, INTERMEDIATES AND USE AS TACHYKININ ANTAGONISTS

This application was filed under 35 U.S.C.§371 based on PCT/EP98/04177 which was filed Jul. 1, 1998 which claims priority from U.K. application serial no. 9714129.5 which was filed on Jul. 4, 1997.

This invention relates to therapeutic agents of the azetidine family. More particularly, this invention relates to azetidinylpropylpiperidine derivatives and to processes for the preparation of, intermediates used in the preparation of, compositions containing and uses of, such derivatives.

International Patent Application Publication Number WO 96/05193 discloses various (azetidin-1-ylalkyl)lactams as tachykinin antagonists.

International Patent Application Publication Number WO97/25322 discloses various azetidinylalkyl derivatives of N-substituted nitrogen heterocycles as tachykinin antagonists. Certain of the compounds and salts of this invention are generically but not specifically described therein.

The present azetidinylpropylpiperidine derivatives are antagonists of tachykinins, including neurokinin A (NKA), neurokinin B (NKB) and Substance P, acting at the human neurokinin-1 ($NK_1$), neurokinin-2 ($NK_2$) or neurokinin-3 ($NK_3$) receptor, or a combination of two or more thereof. They are therefore useful for preventing or treating an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, dyspepsia, irritable bowel syndrome, gastro-oesophageal reflux, faecal incontinence, colitis, ulcerative colitis or Crohn's disease, a disease caused by *Helicobacter pylori* or other urease positive Gram negative bacteria, a urogenital tract disorder such as incontinence, hyperreflexia, impotence or cystitis, a pulmonary disorder such as chronic obstructive airways disease, an allergy such as eczema, contact dermatitis, atopic dermatitis, urticaria, eczematoid dermatitis or rhinitis, a hypersensitivity disorder such as to poison ivy, a vasospastic disease such as angina or Reynaud's disease, a proliferative disorder such as cancer or a disorder involving fibroblast proliferation, a fibrosing or collagen disease such as scleroderma or eosinophillic fascioliasis, reflux sympathetic dystrophy such as shoulder/hand syndrome, an addiction disorder such as alcoholism, a stress-related somatic disorder, a peripheral neuropathy such as diabetic neuropathy, neuralgia, causalgia, painful neuropathy, a burn, herpetic neuralgia or post-herpetic neuralgia, a neuropathological disorder such as Parkinson's disease, Alzheimer's disease or multiple sclerosis, a disorder related to immune enhancement or suppression such as systemic lupus erythematosis, a rheumatic disease such as fibrositis, emesis, cough, acute or chronic pain, migraine, an opthalmic disease such as proliferative retinopathy, occular inflammation, conjunctivitis, a bladder disorder, or a viral disease such as influenza or a cold.

The present derivatives are particularly potent and selective antagonists of tachykinins, including NKA, NKB and Substance P, acting at the human $NK_1$, $NK_2$ and $NK_3$ receptors or combinations of two or more thereof. They are particularly useful for treating or preventing an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, dyspepsia, irritable bowel syndrome, gastro-oesophageal reflux, faecal incontinence, colitis, ulcerative colitis or Crohn's disease, a urogenital tract disorder such as incontinence or cystitis, a neuropathological disorder such as Parkinson's disease, Alzheimer's disease or multiple sclerosis, a pulmonary disorder such as chronic obstructive airways disease, an allergy such as eczema, contact dermatitis or rhinitis, a hypersensitivity disorder such as to poison ivy, a peripheral neuropathy such as diabetic neuropathy, neuralgia, causalgia, painful neuropathy, occular inflammation, conjunctivitis, a bladder disorder, a burn, herpetic neuralgia or post-herpetic neuralgia, cough or acute or chronic pain.

The present invention provides compounds of the formula (I):

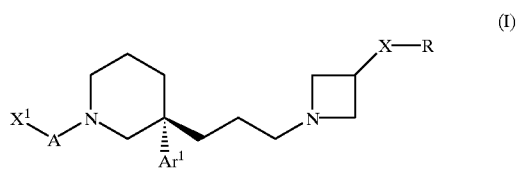

and the pharmaceutically-acceptable salts thereof, wherein

A is CO, $SO_2$ or $CH_2$;

$Ar^1$ is phenyl optionally substituted by one or more substituents independently selected from halogen, $C_{1-6}$ alkoxy optionally substituted by one or more halogen, and $C_{1-6}$ alkyl optionally substituted by one or more halogen;

$X^1$ is $C_{3-7}$ cycloalkyl, aryl or $C_{1-6}$ alkyl,
said $C_{1-6}$ alkyl being optionally substituted by fluoro, $CO_2H$, $CO_2(C_{1-4}$ alkyl), $C_{3-7}$ cycloalkyl, adamantyl, aryl or het,
and said $C_{3-7}$ cycloalkyl being optionally substituted by 1 or 2 substituents each independently selected from $C_{1-4}$ alkyl, $C_{3-7}$ cycloalkyl, $C_{1-4}$ alkoxy, OH, F, fluoro($C_{1-4}$ alkyl) and fluoro($C_{1-4}$ alkoxy);

X is a direct link or $NR^1$;

R is $SO_2$aryl, $SO_2(C_{1-6}$ alkyl optionally substituted by one or more halogen),

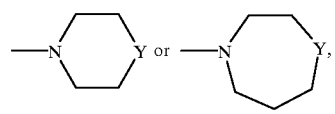

$R^1$ is H or $C_{1-6}$ alkyl optionally substituted by one or more halogen,
or $R^1$ is phenyl optionally substituted by one or more substituents independently selected from halogen, $C_{1-6}$ alkoxy optionally substituted by one or more halogen, or $C_{1-6}$ alkyl optionally substituted by one or more halogen;

Y is O, NCO($C_{1-6}$ alkyl optionally substituted by one or more halogen), $NCO_2(C_{1-6}$ alkyl optionally substituted by one or more halogen), $NSO_2(C_{1-6}$ alkyl optionally substituted by one or more halogen), NCOaryl, $NCO_2$aryl, $NSO_2$aryl, $NSO_2(C_{1-6}$ alkyl optionally substituted by one or more halogen), $CH_2$, CHF, $CF_2$, NH, NCH$_2$aryl, N(C$_{1-6}$ alkyl optionally substituted by one or more halogen), or NCH$_2$(C$_{3-7}$ cycloalkyl);

with the proviso that X is not NR$^1$ when R is

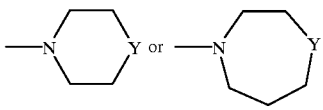

wherein "aryl" used in all the above definitions represents phenyl or naphthyl each optionally substituted with one or more substituents independently selected from halogen, C$_{1-6}$ alkoxy optionally substituted by one or more halogen, and C$_{1-6}$ alkyl optionally substituted by one or more halogen;

and "het" used in the definition of X$^1$ means thienyl or a 5- or 6-membered ring heteroaryl group containing either 1 or 2 nitrogen heteroatoms or 1 nitrogen heteroatom and one oxygen or sulphur heteroatom, each optionally substituted by 1 or 2 substituents each independently selected from C$_{1-4}$ alkyl, C$_{1-4}$ alkoxy, halogen, fluoro(C$_{1-4}$ alkyl) and fluoro(C$_{1-4}$ alkoxy), hereinafter referred to as "substances of the invention".

"Alkyl" groups can be straight or branched chain.

"Halogen" means fluorine, chlorine, bromine or iodine.

"Ph" means phenyl.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts.

Suitable base salts are formed from bases which form non-toxic salts and examples are the aluminium, calcium, lithium, magnesium, potassium, sodium, zinc and diethanolamine salts.

For a review on suitable salts see Berge et al, J. Pharm. Sci., 66, 1–19 (1977).

Preferably, A is CO or SO$_2$. More preferably, A is CO.

Preferably, Ar$^1$ is phenyl optionally substituted by one or more halogen atoms. More preferably, Ar$^1$ is phenyl optionally substituted by up to two halogen atoms. Yet more preferably, Ar$^1$ is phenyl optionally substituted by one or two chlorine atoms. Most preferably, Ar$^1$ is phenyl, 4-chlorophenyl or 3,4-dichlorophenyl.

Preferably X$^1$ is aryl or C$_{1-6}$ alkyl, said C$_{1-6}$ alkyl being optionally substituted by fluoro, CO$_2$H, CO$_2$(C$_{1-4}$alkyl), C$_{3-7}$ cycloalkyl, adamantyl, aryl or het, and said C$_{3-7}$ cycloalkyl being optionally substituted by 1 or 2 substituents each independently selected from C$_{1-4}$ alkyl, C$_{3-7}$ cycloalkyl, C$_{1-4}$ alkoxy, OH, F, fluoro(C$_{1-4}$ alkyl) and fluoro(C$_{1-4}$ alkoxy). More preferably, X$^1$ is C$_{1-6}$ alkyl substituted by C$_{3-7}$ cycloalkyl, said C$_{3-7}$ cycloalkyl being optionally substituted by 1 or 2 substituents each independently selected from C$_{1-4}$ alkyl, C$_{3-7}$ cycloalkyl, C$_{1-4}$ alkoxy, OH, F, fluoro(C$_{1-4}$ alkyl) and fluoro(C$_{1-4}$ alkoxy), or X$^1$ is phenyl optionally substituted by one or more substituents independently selected from halogen and C$_{1-6}$ alkyl optionally substituted by one or more halogen. Yet more preferably, X$^1$ is C$_{1-6}$ alkyl substituted by C$_{3-7}$ cycloalkyl, or is phenyl optionally substituted by one or more substituents independently selected from halogen and C$_{1-3}$ alkyl optionally substituted by one or more halogen. Even more preferably, X$^1$ is (C$_{3-7}$ cycloalkyl)methyl, or phenyl optionally substituted by one or more substituents independently selected from halogen and methyl optionally substituted by one or more halogen. Even yet more preferably, X$^1$ is cyclopropylmethyl or phenyl optionally substituted by one or more fluorine or chlorine atoms. Most preferably, X$^1$ is cyclopropylmethyl, phenyl, 3-chlorophenyl or 3,4-difluorophenyl.

Preferably, X is a direct link or NR$^1$, where R$^1$ is C$_{1-6}$ alkyl optionally substituted by one or more halogen, or R$^1$ is phenyl optionally substituted by one or more substituents independently selected from halogen, C$_{1-6}$ alkoxy optionally substituted by one or more halogen, or C$_{1-6}$ alkyl optionally substituted by one or more halogen. More preferably, X is a direct link or NR$^1$, where R$^1$ is C$_{1-6}$ alkyl optionally substituted by one or more halogen, or R$^1$ is phenyl optionally substituted by one or more halogen substituents. Most preferably, X is a direct link, N-methyl or N-phenyl.

Preferably R is SO$_2$aryl, SO$_2$(C$_{1-6}$ alkyl optionally substituted by one or more halogen),

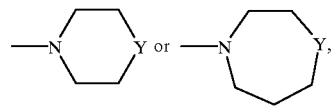

where Y is O, NCO(C$_{1-6}$ alkyl optionally substituted by one or more halogen), NCO$_2$(C$_{1-6}$ alkyl optionally substituted by one or more halogen), NSO$_2$(C$_{1-6}$ alkyl optionally substituted by one or more halogen), NCOaryl, CH$_2$, CHF, CF$_2$, NH, NCH$_2$aryl, N(C$_{1-6}$ alkyl optionally substituted by one or more halogen), or NCH$_2$(C$_{3-7}$ cycloalkyl).

More preferably R is SO$_2$(phenyl optionally substituted with one or more substituents independently selected from halogen, C$_{1-6}$ alkoxy optionally substituted by one or more halogen, or C$_{1-6}$ alkyl optionally substituted by one or more halogen), SO$_2$(C$_{1-3}$ alkyl optionally substituted by one or more halogen),

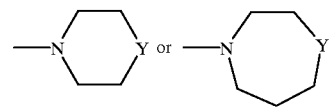

where Y is O, NCO(C$_{1-6}$ alkyl), NCO$_2$(C$_{1-6}$ alkyl), NSO$_2$(C$_{1-6}$ alkyl optionally substituted by one or more halogen), NCO(phenyl optionally substituted with one or more substituents independently selected from halogen, C$_{1-6}$ alkoxy optionally substituted by one or more halogen, or C$_{1-6}$ alkyl optionally substituted by one or more halogen), CHF, CF$_2$, NH, NCH$_2$(phenyl optionally substituted with one or more substituents independently selected from halogen, C$_{1-6}$ alkoxy optionally substituted by one or more halogen, or C$_{1-6}$ alkyl optionally substituted by one or more halogen), N(C$_{1-6}$ alkyl), or NCH$_2$(C$_{3-5}$ cycloalkyl).

Yet more preferably R is SO$_2$Ph, SO$_2$CH$_3$,

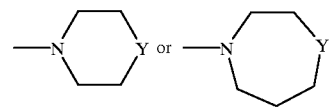

where Y is O, NCOCH$_3$, NCO$_2$C(CH$_3$)$_3$, NSO$_2$CH$_3$, NSO$_2$C$_2$H$_5$, NSO$_2$Ph, NSO$_2$CH$_2$Ph, NSO$_2$CH(CH$_3$)$_2$, NSO₂CH₂CF₃, NCOPh, CHF, NH, NCH₂Ph, or N-cyclopropylmethyl.

Most preferably R is SO₂Ph, SO₂CH₃,

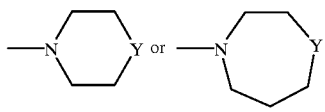

where Y is O, NCOCH₃, NCO₂C(CH₃)₃, NSO₂CH₃, NSO₂C₂H₅, NSO₂Ph, NSO₂CH₂Ph, NSO₂CH(CH₃)₂, NSO₂CH₂CF₃, NCOPh, or CHF.

The most preferred substances of the invention are the compounds mentioned in the Examples below and the salts thereof.

Certain of the compounds of the invention can exist in one or more stereoisomeric forms. The present invention includes all such individual isomers and salts thereof.

Separation of diastereomers may be achieved by conventional techniques, e.g. by fractional crystallisation, chromatography or H.P.L.C. of a stereoisomeric mixture of a compound of formula (I) or a salt thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active base or acid.

The invention further provides synthetic methods for the production of the substances of the invention, which are described below and in the Examples. The skilled man will appreciate that the compounds of the invention could be made by methods other than those herein described, by adaptation of the methods herein described and/or adaptation of methods known in the art, for example the art described herein.

In the Methods below, unless otherwise specified, the substituents are as defined above with reference to the compounds of formula (I) above.

Synthetic Methods

Method 1

The compounds of the invention may be prepared by reaction of a compound of formula (II)

(II)

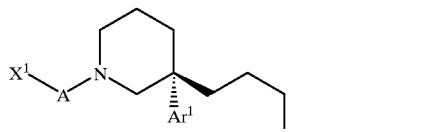

(III)

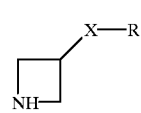

where Z is a suitable leaving group such as methanesulphonate, toluenesulphonate, Cl, Br or I, with a compound of formula (III), optionally in the presence of a base, such as potassium carbonate, preferably in an inert solvent, such as acetonitrile.

The compounds of formulae (II) and (III) may be made by conventional methods, for example by the methods described in the Examples and Preparations, and by adaptation thereof.

Method 2

The compounds of the invention may be prepared by reaction of a compound of formula (IV) with a compound of the formula (III) as defined in Method 1 above, or a salt thereof. The reductive amination reaction is preferably carried out in the presence of a suitable acid, such as acetic acid.

(IV)

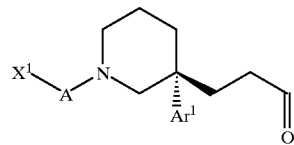

The reaction proceeds via the intitial formation of an intermediate iminium salt of the formula (V), where Y⁻ is the counterion of the acid HY, which salt of the formula (V) may be stable and isolatable.

(V)

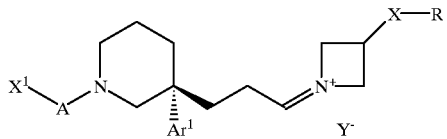

The reaction is preferably carried out without isolation of the intermediate of formula (V) in which case it is reduced in situ to provide a compound of formula (I). In a typical procedure, the aldehyde of formula (IV) is first reacted with the azetidine of formula (III) or salt thereof in a suitable solvent, such as tetrahydrofuran (THF), and the mixture is then treated with a suitable reducing agent, e.g. sodium triacetoxyborohydride or sodium cyanoborohydride, in the presence of a suitable acid, e.g. acetic acid, to give the required product. If an acid addition salt of the azetidine of formula (III) is used as starting material, a suitable acid acceptor, e.g. triethylamine can be added prior to the addition of the reducing agent.

The reaction is typically carried out at room temperature.

The compounds of formula (IV) may be made by oxidation of compounds of formula (II) as described in Method 1 above, where Z is OH. Suitable oxidising systems include the "Swern" system, using oxalyl chloride/methyl sulphoxide in the presence of a base such as diisopropylethylamine.

Method 3

Compounds of formula (I) can be made by reaction of compounds of formula (VI) with compounds of formula (VII), where Z¹ is a suitable leaving group such as is defined above for Z in Method 1.

(VII)

(VI)

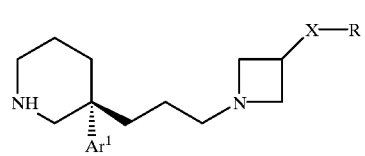

Where A is CO, Z¹ is conveniently Cl, or OCOX¹ (i.e. the reagent is the acid anhydride of X¹CO₂H). The acylation can be carried out using conventional methods, such as in the presence of a suitable base in a suitable sovent. Alternatively, compounds where A is CO can be conveniently prepared by reaction of a compound of formula (VI) with an acid of formula (VII) where $Z^1$ is OH, in a "peptide coupling" reaction, such as is described by R C Larock in "Comprehensive Organic Transformations—A Guide to Functional Group Preparations", VCH (1989), and references therein.

Where A is $CH_2$, the alkylation can be carried out by conventional methods, such as by reaction of the compound of formula (VI) with an species of formula (VII) where $Z^1$ is a suitable leaving group such as Cl, Br, I, methanesulphonate or toluenesulphonate, optionally in the presence of a suitable base such as triethylamine.

Where A is $SO_2$, the reaction can suitably be carried out with a species of formula (VII) where $Z^1$ is a suitable leaving group such as Cl, Br, I, methanesulphonate or toluenesulphonate, optionally in the presence of a suitable base such as triethylamine.

Method 4

Piperidine compounds of formula (I) can be prepared by reduction of the corresponding lactams of formula (VIII), for example by reaction with a suitable hydride reducing agent such as are described in R C Larock in "Comprehensive Organic Transformations—A Guide to Functional Group Preparations", VCH (1989), pp.432–434, and references therein.

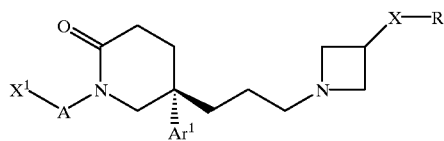

(VIII)

Compounds of formula (VIII) can be made by methods described in WO 96/05193 and adaptation thereof by methods known in the art.

Method 5

Compounds of formula (I) can be prepared by reaction of compounds of formula (IX), where $Z^2$ is a leaving group and corresponds to Z as defined in Method 1 above, with a nucleophilc reagent acting as a $RX^-$ "synthon".

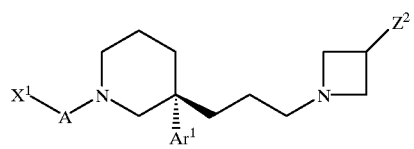

(IX)

Suitably, $Z^2$ is methanesulphonate, and the reaction is carried out by generation of the $RX^-$ moiety by e.g. reaction of the corresponding RXH compound with a base such as an alkyllithium base, optionally in the presence of an inert solvent. Alternatively the RXH compound may itself be nucleophilic enough to displace the $Z^2$ group without first converting it to the anion $RX^-$.

Compounds of formula (IX) can be prepared by adaptation of methods described herein and in the art described herein, by methods known to the skilled chemist.

Method 6

Compounds of formula (I) may be prepared from compounds of formula (X) where $Z^3$ and $Z^4$ are leaving groups independently defined as Z in Method 1, with a reagent of formula $X^1$—A—$NH_2$.

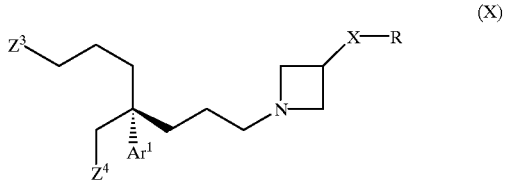

(X)

Compounds of formulae (X) and $X^1$—A—$NH_2$ may be prepared by conventional methods, such as by adaptation of methods described herein, and in the art described herein.

Method 7

Compounds of the formula (I) where R is

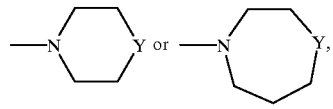

where Y is $NCO(C_{1-6}$ alkyl optionally substituted by one or more halogen), $NCO_2(C_{1-6}$ alkyl optionally substituted by one or more halogen), $NSO_2(C_{1-6}$ alkyl optionally substituted by one or more halogen), NCOaryl, $NCO_2$aryl, $NSO_2$aryl, $NSO_2(C_{1-6}$ alkyl optionally substituted by one or more halogen), $NCH_2$aryl, $N(C_{1-6}$ alkyl optionally substituted by one or more halogen), or $NCH_2(C_{3-7}$ cycloalkyl), can be made by reaction of a compound of formula (I) where R is

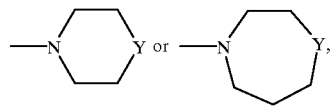

as appropriate, and Y is NH, with a reagent of formula [($C_{1-6}$ alkyl optionally substituted by one or more halogen)CO—, ($C_{1-6}$ alkyl optionally substituted by one or more halogen)$CO_2$—, ($C_{1-6}$ alkyl optionally substituted by one or more halogen)$SO_2$—, arylCO—, aryl$CO_2$—, aryl$SO_2$—, ($C_{1-6}$ alkyl optionally substituted by one or more halogen)$SO_2$—, aryl$CH_2$—, ($C_{1-6}$ alkyl optionally substituted by one or more halogen)-, or ($C_{3-7}$ cycloalkyl)$CH_2$—]—$Z^5$, where $Z^5$ is a suitable leaving group such as chloride, bromide, iodide, methanesulphonate, toluenesulphonate, etc., optionally in the presence of a base such as triethylamine, preferably in the presence of an inert solvent.

Method 8

Compounds of the formula (I) where R is

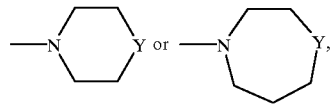

where Y is NH can be conveniently prepared by reaction of a corresponding compound where Y is $NCO_2(C(CH_3)_3)$, with an acid, such as trifluoroacetic acid, preferably in the presence of an inert solvent.

Where desired or necessary, the compound of formula (I) can be converted into a pharmaceutically acceptable salt thereof, conveniently by mixing together solutions of a compound of formula (I) and the desired acid or base, as appropriate, the salt may be precipitated from solution and collected by filtration, or may be collected by other means such as by evaporation of the solvent.

It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

It will be apparent to those skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1991).

The compounds of the invention may be purified by conventional methods.

The affinity of the compounds of formula (I) and their salts for the human $NK_1$ receptor can be tested in vitro by testing their ability to inhibit [$^3$H]-Substance P binding to membranes prepared from the human IM9 cell line expressing the human $NK_1$ receptor using a modification of the method described in McLean, S. et al, J. Pharm. Exp. Ther., 267, 472–9 (1993) in which whole cells were used.

The affinity of the compounds of formula (I) and their salts for the human $NK_2$ receptor can be tested in vitro by testing their ability to compete with [$^3$H] or [$^{125}$I]NKA (neurokinin A) for binding to membranes prepared from Chinese hamster ovary cells expressing the cloned human $NK_2$ receptor. In this method, washed Chinese hamster ovary cell membranes are prepared as described for the previous method where IM9 cells are used instead. The membranes are incubated (90 min, 25° C.) with [$^3$H] or [$^{125}$I] NKA and with a range of concentrations of the test compound. Non-specific binding was determined in the presence of 10 $\mu$M NKA.

The $NK_2$ receptor antagonist activity of the compounds of the formula (I) can be tested, in vitro, by testing their ability to antagonise the contractile effects of the selective $NK_2$ receptor agonist [$\beta$Ala$^8$]NKA$_{(4-10)}$ in the rabbit pulmonary artery, using the method of Patacchini and Maggi, Eur. J. Pharmacol., 236, 31–37 (1993).

The compounds of the formula (I) and their salts can be tested for $NK_2$ receptor antagonist activity, in vivo, by testing their ability to inhibit bronchoconstriction induced by [$\beta$Ala$^8$]NKA$_{(4-10)}$ in the anaesthetised guinea pig, using the method described by Murai et al, J. Pharm. Exp. Ther., 262, 403–408 (1992) or Metcalfe et al, Br. J. Pharmacol., 112, 563P (1994).

The compounds of the formula (I) and their salts can be tested for $NK_3$ receptor antagonist activity, in vitro, by testing their ability to antagonise the contractile effects of the selective $NK_3$ receptor agonist senktide in the guinea-pig ileum using the method of Maggi et al, Br. J. Pharmacol., 101, 996–1000 (1990).

The affinity of the compounds of formula (I) and their salts for the $NK_3$ receptor can be tested in vitro by testing their ability to displace [$^3$H] senktide at the guinea pig cortex $NK_3$ receptor. The receptors are prepared by the method described by S. Guard, et al, in Br.J.Pharmacol. (1990), 99, 767.

For human use, the compounds of the formula (I) and their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) and their salts will be from 0.001 to 20, preferably from 0.01 to 20, more preferably from 0.1 to 10, and most preferably from 0.5 to 5, mg/kg (in single or divided doses). Thus tablets or capsules of the compounds will contain from 0.1 to 500, preferably from 50 to 200, mg of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilisers and preservatives as may be required.

It is to be appreciated that reference to treatment includes prophylaxis as well as the alleviation of established symptoms of the disease.

The invention further provides:

i) a pharmaceutical composition comprising a substance of the invention together with a pharmaceutically acceptable diluent or carrier;

ii) a substance of the invention or composition thereof, for use as a medicament;

iii) the use of a substance of the invention or composition thereof, for the manufacture of a medicament for the treatment of a disease by producing an antagonist effect on a tachykinin acting at the human $NK_1$, $NK_2$ or $NK_3$ receptor, or a combination of two or more thereof;

iv) use as in (iii) where the disease is an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, dyspepsia, irritable bowel syndrome, gastro-oesophageal reflux, faecal incontinence, colitis, ulcerative colitis or Crohn's disease, a disease caused by *Helicobacter pylori* or other urease positive Gram negative bacteria, a urogenital tract disorder such as incontinence, hyperreflexia, impotence or cystitis, a pulmonary disorder such as chronic obstructive airways disease, an allergy such as eczema, contact dermatitis, atopic dermatitis, urticaria, eczematoid dermatitis or rhinitis, a hypersensitivity disorder such as to poison ivy, a vasospastic disease such as angina or Reynaud's disease, a proliferative disorder such as cancer or a disorder involving fibroblast proliferation, a fibrosing or collagen disease such as scleroderma or eosinophillic fascioliasis, reflux sympathetic dystrophy such as shoulder/hand syndrome, an addiction disorder such as alcoholism, a stress-related somatic disorder, a peripheral neuropathy such as diabetic neuropathy, neuralgia, causalgia, painful neuropathy, a burn, herpetic neuralgia or post-herpetic neuralgia, a neuropathological disorder such as Parkinson's disease, Alzheimer's disease or multiple sclerosis, a disorder related to immune enhancement or suppression such as systemic lupus erythematosis, a rheumatic disease such as fibrositis, emesis, cough, acute or chronic pain, migraine, an opthalmic disease such as proliferative retinopathy, ocular inflammation, conjunctivitis, a bladder disorder, or a viral disease such as influenza or a cold;

v) a method of treatment of a human to treat a disease by producing an antagonist effect on a tachykinin acting at the human $NK_1$, $NK_2$ or $NK_3$ receptor, or a combination of two or more thereof, which comprises treating said human with an effective amount of a substance of the invention or composition thereof;

vi) a method as in (v) where the disease is an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, dyspepsia, irritable bowel syndrome, gastro-oesophageal reflux, faecal incontinence, colitis, ulcerative colitis or Crohn's disease, a disease caused by *Helicobacter pylori* or other urease positive Gram negative bacteria, a urogenital tract disorder such as incontinence, hyperreflexia, impotence or cystitis, a pulmonary disorder such as chronic obstructive airways disease, an allergy such as eczema, contact dermatitis, atopic dermatitis, urticaria, eczematoid dermatitis or rhinitis, a hypersensitivity disorder such as to poison ivy, a vasospastic disease such as angina or Reynaud's disease, a proliferative disorder such as cancer or a disorder involving fibroblast proliferation, a fibrosing or collagen disease such as scleroderma or eosinophillic fascioliasis, reflux sympathetic dystrophy such as shoulder/hand syndrome, an addiction disorder such as alcoholism, a stress-related somatic disorder, a peripheral neuropathy such as diabetic neuropathy, neuralgia, causalgia, painful neuropathy, a burn, herpetic neuralgia or post-herpetic neuralgia, a neuropathological disorder such as Parkinson's disease, Alzheimer's disease or multiple sclerosis, a disorder related to immune enhancement or suppression such as systemic lupus erythematosis, a rheumatic disease such as fibrositis, emesis, cough, acute or chronic pain, migraine, an opthalmic disease such as proliferative retinopathy, ocular inflammation, conjunctivitis, a bladder disorder, or a viral disease such as influenza or a cold;

vii) the synthetic methods herein described, and viii) certain novel intermediates herein described.

The following Examples illustrate the preparation of the substances of the invention.

In the Examples and Preparations which follow, $^1$H NMR data are presented in parts per million shift from tetramethylsilane (δ), and are measured in solution in $CDCl_3$ unless specified otherwise. Thin layer chromatography (TLC) was carried out using Merck kieselgel™ silica plates, unless otherwise specified. In the structures which follow "Me" and "Ph" represent a methyl and phenyl group respectively.

EXAMPLE 1

(+)-3(R)-1-Benzoyl-3-(3-[3-(4-tert-butoxycarbonylpiperazin-1-yl)azetidin-1-yl]propyl)-3-(3,4-dichlorophenyl)piperidine

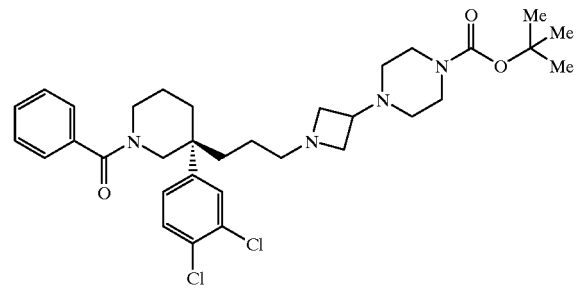

A mixture of the compounds of PREPARATION 8 (11.62 g) and PREPARATION 10 (14 g) and potassium carbonate (10.23 g) in dry acetonitrile (300 mL) was heated, with vigourous stirring, under reflux for 18 hours. The cooled mixture was diluted with ethyl acetate (700 mL) and washed with 50% aqueous sodium chloride solution (70 mL). The organic solution was dried over sodium sulphate and evaporated to dryness in vacuo. The residue was purified by column chromatography over silica gel using gradient elution (dichloromethane/methanol/ammonium hydroxide 93/7/1 to 80/20/3) to afford the title compound (15.36 g) and recovered compound from PREPARATION 10 (5.85 g).

TLC $R_f$: 0.15 (dichloromethane/methanol 95/5 by volume).

LRMS m/z: 616 (MH$^+$).

$^1$H NMR: 7.38 (m, 4H), 7.21 (m, 4H), 4.52 (br s, 1H), 3.38 (m, 9H), 2.90 (m, 1H), 2.72 (m, 2H), 2.37–2.03 (m, 8H), 1.80 (m, 1H), 1.60 (m, 2H), 1.42 (s, 9H), 1.20 (m, 1H), 0.93 (m, 2H).

Found: C, 63.32; H, 7.21; N, 9.05. $C_{33}H_{44}Cl_2N_4O_3$.3/20$CH_2Cl_2$ requires C, 63.36; H, 7.11; N, 8.92%.

$[a]_D$+16.2° (c=0.13, methanol).

EXAMPLE 2

3(R)-1-Benzoyl 3-(3-[3-(4-tert-butoxycarbonylhomopiperazin-1-yl)azetidin-1-yl] propyl)-3-(3,4-dichlorophenyl)piperidine The compounds from PREPARATION 8 (470 mg) and PREPARATION 12 (260 mg) were mixed with potassium carbonate (414 mg) in acetonitrile (15 mL) and heated to reflux overnight. The reaction mixture was allowed to cool and was partitioned between ethyl acetate and water. The organic phase was washed with brine, dried over magnesium sulphate, and filtered to give a crude material which was subsequently purified by silica gel chromatography with dichloromethane:methanol (98:2) eluant to give pure product (334 mg).

$^1$H NMR: 7.35–7.2 (m, 8H), 3.45–3.37 (m, 13H), 2.59–2.06 (m, 6H), 1.74–1.40 (m, 10H).

LRMS m/z 630 (m+H)$^+$

EXAMPLE 3

(+)-3(R)-1-Benzoyl-3-(3,4-dichlorophenyl)-3-(3-[3-(4-methanesulphonylpiperazin-1-yl)azetidin-1-yl] propyl)piperidine

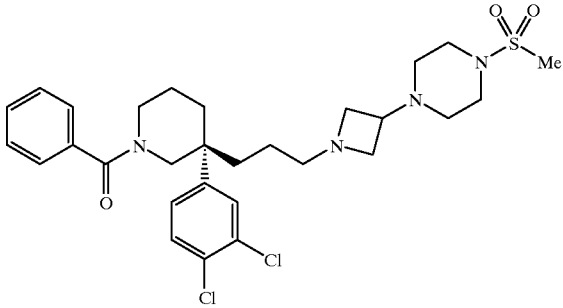

A solution of methanesulphonyl chloride (122 μl) in dichloromethane (15 mL) was added over a period of 30 minutes to an ice-cold solution of the compound of PREPARATION 13 (773 mg) and triethylamine (420 μl) in dichloromethane (30 mL) under nitrogen and the mixture stirred for 1 hour. The reaction mixture was evaporated to dryness in vacuo and the residue was purified by column chromatography over silica gel (dichloromethane/methanol/ammonium hydroxide 95/5/0.5) to afford the title compound as a foam (740 mg).

TLC $R_f$: 0.41 (dichloromethane/methanol/ammonium hydroxide 93/7/1 by volume).

m/z: 593 (MH$^+$).

$^1$H NMR: 7.38 (m, 5H), 7.20 (m, 3H), 4.48 (m, 1H), 3.60–3.08 (m, 8H), 2.92 (m, 1H), 2.70 (m, 5H), 2.30 (m, 6H), 2.10 (br s, 1H), 1.78 (m, 1H), 1.68–1.05 (m, 6H), 0.90 (m, 1H).

Found: C, 56.77; H, 6.19; N, 9.03. $C_{29}H_{38}Cl_2N_4O_3S$.3/10CH$_2$Cl$_2$ requires C, 56.84; H, 6.28; N, 9.05%.

$[a]_D$+20.3° (c=0.12, methanol).

EXAMPLE 4

(+)-3(R)-3-(3-[3-(4-Acetylpiperazin-1-yl)azetidin-1-yl]propyl)-1-benzoyl-3-(3,4-dichlorophenyl) piperidine

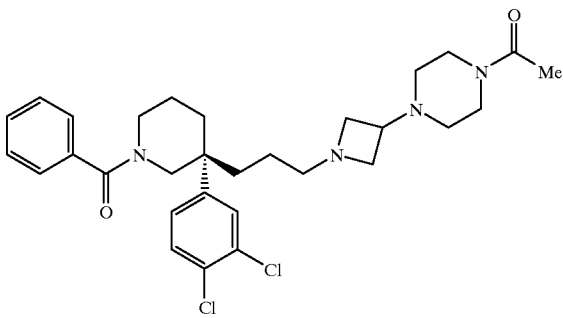

A solution of acetic anhydride (104 μl) in dichloromethane (20 mL) was added to an ice-cold solution of the compound of PREPARATION 13 (515 mg) and triethylamine (280 μl) in dichloromethane (25 mL). The reaction mixture was allowed to warm to room temperature and stirring was continued for 2 hours. The reaction mixture was evaporated to dryness in vacuo and the residue purified by column chromatography over silica gel using gradient elution (dichloromethane/methanol/ammonium hydroxide 95/5/0.5 to 93/7/1 by volume) to afford the title compound as a foam (458 mg).

TLC $R_f$: 0.33 (dichloromethane/methanol/ammonium hydroxide 93/7/1 by volume).

m/z: 556 (MH$^+$).

$^1$H NMR: 7.50–7.00 (m, 8H), 4.40 (br s, 1H), 3.55 (m, 3H), 3.43–3.00 (m, 8H), 2.85 (m, 1H), 2.70 (br s, 2H), 2.37–1.82 (m, 6H), 1.82–1.01 (m, 8H), 0.88 (m, 1H).

Found: C, 62.75; H, 6.93; N, 9.61. $C_{30}H_{38}Cl_2N_4O_2$.1/4CH$_2$Cl$_2$ requires C, 62.75; H, 6.93; N, 9.68%.

$[a]_D$+20.4° (c=0.102, methanol).

EXAMPLE 5

(+)-3(R)-1-Benzoyl-3-(3-[3-(4-Benzoylpiperazin-1-yl)azetidin-1-yl]propyl)-3-(3,4-dichlorophenyl) piperidine

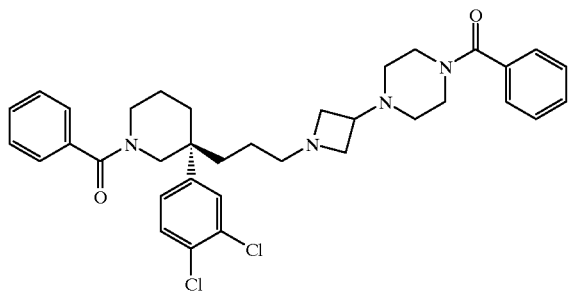

A solution of benzoyl chloride (128 μl) in dichloromethane (15 mL) was added to a solution of the compound of PREPARATION 13 (516 mg) and triethylamine (280 μl) in dichloromethane (25 mL). The reaction mixture was stirred for 2 hours at room temperature. The reaction mixture was evaporated to dryness in vacuo and the residue was purified by column chromatography over silica gel (dichloromethane/methanol/ammonium hydroxide 95/5/0.5 by volume) to afford the title compound as a foam (489 mg).

TLC $R_f$: 0.49 (dichloromethane/methanol/ammonium hydroxide 93/7/1 by volume).

m/z: 618 (MH$^+$).

$^1$H NMR: 7.48–7.13 (m, 13H), 4.43 (m, 1H), 3.73 (m, 2H), 3.45–3.05 (m, 7H), 2.90 (m, 1H), 2.72 (m, 2H), 2.39–2.01 (m, 7H), 1.78 (t, 1H), 1.67–1.05 (m, 5H), 0.90 (m, 1H).

Found: C, 66.00; H, 6.45; N, 8.69. $C_{35}H_{40}Cl_2N_4O_2$.1/4CH$_2$Cl$_2$ requires C, 66.06; H, 6.37; N, 8.74%.

$[a]_D$+15.2° (c=0.14, methanol).

EXAMPLES 6–10

The following compounds of the general formula:

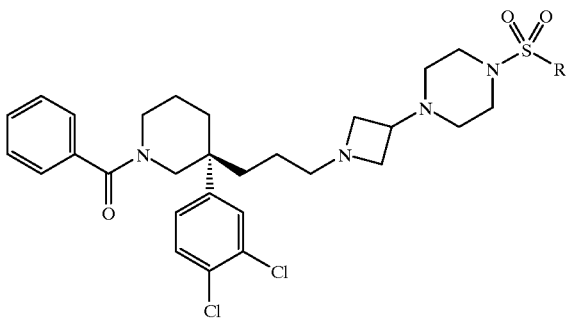

or salts thereof, were prepared from the compound of Preparation 13 and the corresponding sulphonyl chlorides by similar methods to that used in Example 3.

EXAMPLE 6

(+)-3(R)-1-Benzoyl-3-(3,4-dichlorophenyl)-3-(3-[3-(4-methanesulphonylpiperazin-1-yl)azetidin-1-yl] propylpiperidine

EXAMPLE 7

(+)-3(R)-3-(3-[3-(4-Benzenesulphonylpiperazin-1-yl)azetidin-1-yl]propyl)-1-benzoyl-3-(3,4-dichlorophenyl)piperidine

EXAMPLE 8

(+)-3(R)-1-Benzoyl-3-(3-[3-(4-benzylsulphonylpiperazin-1-yl)azetidin-1-yl]propyl)-3-(3,4-dichlorophenyl)piperidine

EXAMPLE 9

(+)-3(R)-1-Benzoyl-3-(3,4-dichlorophenyl)-3-(3-[3-(4-iso-propylsulphonylpiperazin-1-yl)azetidin-1-yl] propyl)piperidine

EXAMPLE 10

(+)-3(R)-1-Benzoyl-3-(3,4-dichlorophenyl)-3-(3-[3-(4-(2,2,2-trifluoroethane)sulphonylpiperazin-1-yl) azetidin-1-yl]propyl)piperidine

| Example No. | R | m/z | Rf * | $[\alpha]_D$ methanol | Analysis/$^1$H NMR |
|---|---|---|---|---|---|
| 6 | $C_2H_5$ | 607 | 0.38 | +17.3°<br>c = 0.102 | $\delta_H$: 7.35(m,4H),<br>7.20(m,4H),<br>4.49(br s,1H),<br>3.28(m,8H),<br>2.90(m,3H),<br>2.68(m,2H),<br>2.30(m,6H),<br>2.10(m,1H),<br>1.88(t,1H),<br>1.56(m,4H),<br>1.38(m,1H),<br>1.32(t,3H),<br>1.18(m,1H),<br>0.90(m,1H), |
| 7 | Ph | 6.54 | 0.47 | +13.8°<br>c = 0.12 | Found: C, 58.33; H, 6.62; N, 9.05. $C_{28}H_{40}Cl_2N_4O_3S$.3/20$CH_2Cl_2$ requires C, 58.37; H, 6.55; N, 9.03%<br>$\delta_H$: 7.71(m,2H),<br>7.52(m,3H),<br>7.37(m,4H),<br>7.18(m,4H),<br>4.48(m,1H),<br>3.50–3.08(m,5H),<br>3.30(m, 5H),<br>2.85(t,1H),<br>2.59(m,2H),<br>2.32(m,3H),<br>2.20(m,2H),<br>2.08(m,1H),<br>1.75(t,1H),<br>1.65–1.37(m, 4H), 1.14(,1H),<br>0.85(m,1H). |
| 8 | $PhCH_2$ | 669 | 0.48 | +15.2°<br>c = 0.104 | Found: C, 61.45; H, 6.15; N, 8.33. $C_{34}H_{40}Cl_2N_4O_3S$.1/10$CH_2Cl_2$ requires C, 61.67; H, 6.10; N, 8.44%<br>$\delta_H$: 7.40–7.12(m,13H),<br>4.48(m,1H),<br>4.15(s,2H),<br>3.48–3.20(m,4H),<br>3.09(m,4H),<br>2.84(m,1H),<br>2.63(m,2H),<br>2.30–2.02(m,7H),<br>1.78(t,1H)<br><1.63–1.28(m,5H),<br>1.15(m,1H),<br>0.88(m,1H). |
| 9 | $CH(CH_3)_2$ | 621 | 0.42 | +21.5°<br>c = 0.104 | Found: C, 60.65; H, 6.22; N, 8.00. $C_{35}H_{42}Cl_2N_4N_3S$.2/5$CH_2Cl_2$ requires C, 60.42; H, 6.13; N, 7.06%<br>$\delta_H$: 7.40(m,4H),<br>7.27(m,4H),<br>4.50(m,1H),<br>3.37(m,8H),<br>3.18(m,1H),<br>2.95(m,1H),<br>2.75(m,2H),<br>2.36(m,6H),<br>2.14(m,1H),<br>1.90–0.90(m,8H),<br>1.35(d,6H). |
| 10 | $CF_3CH2$ | 661 | 0.44 | +21.0°<br>c = 0.12 | Found: C, 58.84; H, 6.79; N, 8.74. $C_{31}H_{42}Cl_2N_4O_3S$.1/5$CH_2Cl_2$ requires C, 58.68; H, 6.69; N, 8.77%<br>$\delta_H$: 7.48(m,4H),<br>7.17(m,4H),<br>4.48(m,1H),<br>3.67(m,3H),<br>3.30(m,8H),<br>2.91(t,1H),<br>2.68(m,2H),<br>2.30(m,6H),<br>2.10(m,1H),<br>1.79(m,1H),<br>1.58(m,3H),<br>1.38(m,1H),<br>1.18(m,1H), |

-continued

| Example No. | R | Rf m/z | [α]$_D$ * methanol | Analysis/$^1$H NMR |
|---|---|---|---|---|
| | | | | 0.90(m,1H). Found: C, 53.66; H, 5.57; N, 8.23. C$_{30}$H$_{37}$Cl$_2$F$_3$N$_4$O$_3$S.3/10CH$_2$Cl$_2$ requires C, 53.70; H, 5.58; N, 8.31% |

TLC: dichloromethane/methanol/ammonium hydroxide 93/7/1 by volume

EXAMPLE 11

(+)-3(R)-1-Benzoyl-3-(3,4-dichlorophenyl)-3-(3-[3-morpholinoazetidin-1-yl]propyl)piperidine

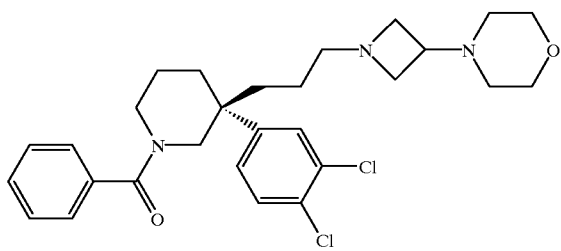

Part A.

Oxalyl chloride (0.17 mL) was added to dichloromethane (10 mL) under nitrogen and the solution cooled in a dry ice/acetone bath before adding anhydrous methyl sulphoxide (0.18 mL) dropwise and allowing to stir for 0.75 h; to this was added the compound from PREPARATION 7 (500 mg) dissolved in dichloromethane (10 mL) dropwise. After an additional 0.75 h, diisopropylethylamine (0.67 mL) was added and the mixture allowed to warm to ambient temperature before pouring into 2 N aqueous hydrochloric acid (75 mL). The resulting solution was extracted with dichloromethane three times. The combined organic phases were washed with brine and dried over sodium sulphate before concentrating to yield the crude aldehyde intermediate as a yellow oil (LRMS m/z 390 [m]$^+$) which was taken on to the next stage without purification.

Part B.

The crude aldehyde from part A was dissolved in tetrahydrofuran (25 mL) along with glacial acetic acid (0.87 mL), sodium triacetoxyborohydride (432 mg), and 3-morpholinoazetidine dihydrochloride (Preparation 25, 411 mg) After stirring the mixture at ambient temperature for 12 h, water (2 mL) was added and the solvent evaporated in vacuo. To the resulting crude product was added 1 N aqueous sodium hydroxide (ca. 10 mL) and this mixture was extracted with dichloromethane three times. The combined organic layers were washed with brine, dried over sodium sulphate, and concentrated in vacuo before purification on silica gel with dichloromethane:methanol:ammonium hydroxide (95:5:0.5) as eluant to yield 553 mg of the desired compound.

$^1$H NMR: 7.5–7.2 (m, 8H), 4.43 (m, 1H), 3.62 (m, 4H), 3.5–3.1 (m, 5H), 2.89 (m, 1H), 2.71 (m, 2H), 2.38–2.2 (m, 6H), 2.07 (m, 1H), 1.79 (m, 1H), 1.1–1.72 (m, 5H), 0.96 (m, 1H).

[α]$_D^{25}$=+22.6° (c=0.1 mg/mL in MeOH).

LRMS m/z 517 (m+H)$^+$.

Found: C, 63.50; H, 6.84; N, 7.81. C$_{28}$H$_{35}$N$_3$O$_2$Cl$_2$.0.18CH$_2$Cl$_2$ requires: C, 63.65, H, 6.70, N, 7.90.

EXAMPLE 12

(+)-3(R)-1-Benzoyl-3-(3,4-dichlorophenyl)3-(3-[3-(N-Methyl benzenesulphonamido)azetidin-1-yl]propyl)piperidine

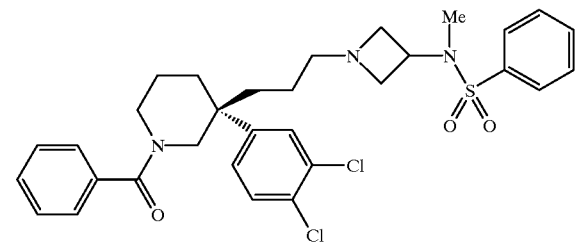

The compound from PREPARATION 8 (225 mg) was mixed with the compound from PREPARATION 20 (250 mg) and potassium hydrogen carbonate (200 mg) in acetonitrile (15 mL) and the resulting mixture was heated to reflux overnight. After cooling the reaction to ambient temperature, water (15 mL) was added and the mixture was extracted three times with ethyl acetate. The combined organic layers were washed with brine, dried over magnesium sulphate, and concentrated in vacuo. Purification of the crude product on silica gel with ethyl acetate:2-propanol (4:1) as eluant yielded the title compound (165 mg).

$^1$H NMR: 7.70 (m, 1H), 7.49 (m, 2H), 7.31 (m, 2H), 7.18 (m, 3H), 4.42 (m, 1H), 3.82 (m, 1H), 3.50–3.09 (m, 5H), 2.80 (m, 2H), 2.60 (br s, 3H), 2.20 (m, 2H), 2.08 (m, 1H), 1.78 (br t, 1H), 1.70–1.08 (m, 5H), 0.85 (m, 1H).

[α]$_D^{25}$=+20.4° (c=1.0 mg/mL in MeOH).

TLC (ethyl acetate:2-propanol 4:1) R$_f$=0.25.

LRMS m/z 601 (m+H)$^+$

EXAMPLE 13

(+)-3(R)-1-Benzoyl-3-(3,4-dichlorophenyl)-3-(3-[3-N-phenyl methanesulphonamido)azetidin-1-yl]propyl)piperidine

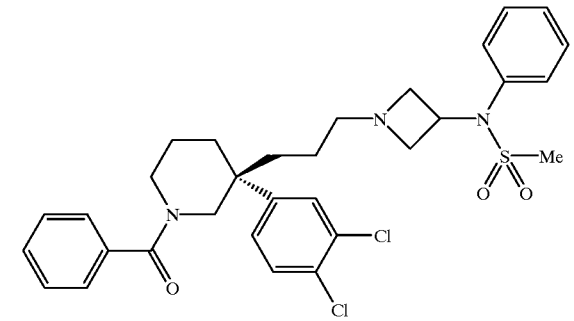

The compound from PREPARATION 8 (300 mg) was mixed with the compound from PREPARATION 22 (400 mg) and potassium hydrogen carbonate (300 mg) in acetonitrile (15 mL) and the resulting mixture was heated to reflux overnight. After cooling the reaction to ambient temperature, water (25 mL) was added and the mixture was extracted three times with ethyl acetate. The combined organic layers were washed with brine, dried over magnesium sulphate, and concentrated in vacuo. Chromatography of the crude product on silica gel with ethyl acetate:2-propanol (4:1) as eluant yielded the title compound (185 mg).

$^1$H NMR: 7.39–7.28 (m, 8H), 7.22–7.17 (m, 5H), 4.46 (m, 2H), 3.55–3.08 (m, 5H), 2.76 (s, 3H), 2.68–2.58 (m, 2H), 2.20–2.02 (m, 3H), 1.72 (m, 1H), 1.60–1.28 (m, 4H), 1.19–1.00 (m, 1H), 0.83 (m, 1H).

$[a]_D^{25}$=+13.8° (c=1.0 mg/mL in MeOH).

TLC (ethyl acetate:2-propanol 4:1) $R_f$=0.20

LRMS m/z 601 (m+H)$^+$

Found: C, 61.05; H, 5.92; N, 6.87. $C_{31}H_{35}N_3O_3Cl_2S.0.5H_2O$ requires: C, 61.08; H, 5.95; N, 6.89

EXAMPLE 14

3(R)-1-Benzoyl-3-(3,4-dichlorophenyl)3-(3-[3-(4-methanesulphonylhomopiperazin-1-yl)azetidin-1-yl]propyl)-piperidine

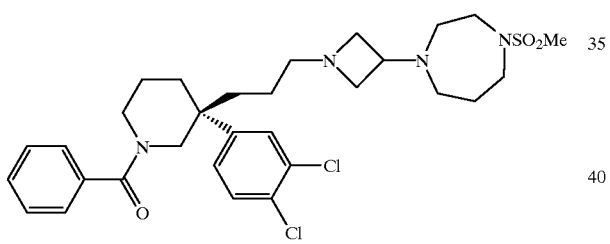

The compound from PREPARATION 14 (100 mg) was dissolved in dichloromethane (2 mL) and cooled in an ice/water bath. To this were added methanesulphonyl chloride (0.02 mL) and triethylamine (0.032 mL). The reaction mixture was allowed to warm to ambient temperature and was stirred overnight before quenching with water. The organic phase was separated, washed with brine, dried with magnesium sulphate, filtered, and concentrated. Silica gel chromatography using dichloromethane:methanol (9:1) eluant yielded the title compound (28 mg).

$^1$H NMR: 7.48–7.22 (m, 8H), 3.4–1.2 (m, 32H).

TLC (dichloromethane:methanol=9:1) $R_f$=0.46.

LRMS m/z 608 (m+H)$^+$.

Found: C, 57.57; H, 6.56; N, 8.42. $C_{30}H_{40}N_4O_3Cl_2S.0.5H_2O.0.33CH_2Cl_2$ requires: C, 57.31; H, 6.45; N, 8.81.

EXAMPLE 15

3(R)-1-Benzenesulphonyl-3-(3,4-dichlorophenyl)3-(3-[3-(4-methanesulphonylpiperazin-1-yl)azetidin-1-yl]propyl)-piperidine

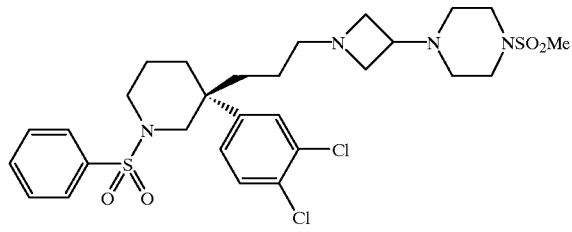

The compound from PREPARATION 18 (125 mg) was dissolved in dichloromethane (2.5 mL) and cooled in an ice/water bath. To this were added triethylamine (0.046 mL) and benzenesulphonyl chloride (0.04 mL). The reaction mixture was allowed to warm to ambient temperature and stirred overnight before quenching with water. The organic phase was separated, washed with brine, dried with magnesium sulphate, filtered, and concentrated. Silica gel chromatography using dichloromethane:methanol (95:5) eluant yielded the title compound (52 mg).

$^1$H NMR: 7.73 (m, 2H), 7.55 (m, 1H), 7.50 (m, 2H), 7.37 (m, 1H), 7.20 (m, 1H), 3.46–0.84 (m, 30H)

TLC (dichloromethane:methanol=9:1) $R_f$=0.45

LRMS m/z 630 (m+H)$^+$

Found: C, 52.35; H, 6.11; N, 8.46. $C_{28}H_{38}N_4O_4Cl_2S_2.0.2H_2O$ requires: C, 52.38; H, 5.99; N, 8.34.

EXAMPLE 16

(+)-3(R)-1-(Cyclopropylacetyl)-3-(3,4-dichorophenyl 3-(3-[3-(4-methanesulphonylpiperazin-1-yl)azetidin-1-yl]propyl)piperidine

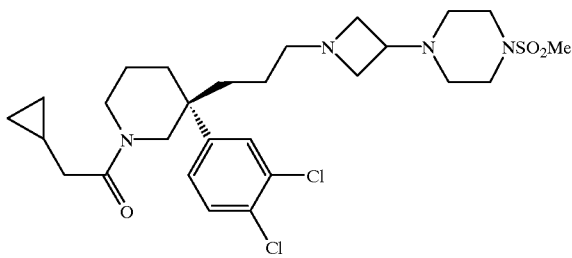

Cyclopropylacetic acid (0.2 mL) was dissolved in dichloromethane (5 mL) and cooled in an ice/water bath. To this were added N-methyl morpholine (0.1 mL), 1-(3-dimethylaminopropyl)-3-ethylcarbodiimide hydrochloride (95 mg), and 1-hydroxybenzotriazole hydrate (50 mg). The compound from PREPARATION 18 (150 mg) was then added after one hour, and the mixture stirred overnight at ambient temperature. The solvent was then evaporated in vacuo, and the mixture partitioned between ethyl acetate and water. The resulting organic phase was washed with brine, dried with magnesium sulphate, filtered, and concentrated. Silica gel chromatography using dichloromethane:methanol (95:5) eluant yielded the title compound.

¹H-NMR: 7.36–7.13 (m, 3H), 3.50–0.79 (m, 37H)

LRMS m/z 572 (m+H)⁺

$[a]_D^{25}$=+42.21° (c=1.0 mg/mL in MeOH)

Found: C, 55.33; H, 7.05; N, 9.47. $C_{27}H_{40}N_4O_3SCl_2 \cdot 0.25CH_2Cl_2$

Requires: C, 55.21, H, 6.89, N, 9.45

EXAMPLE 17

(+)-3(R)-3-(3,4-Dichlorophenyl)-1-(3,4-difluorobenzoyl)-3-(3-[3-(4-methanesulphonylpiperazin-1-yl)azetidin-1-yl]propyl)piperidine

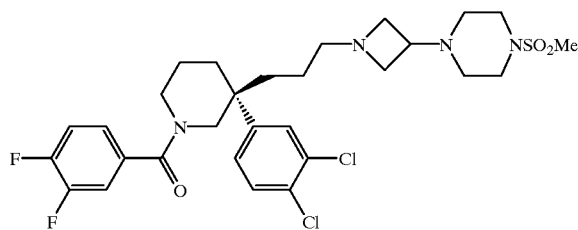

3,4-Difluorobenzoic acid (145 mg) was dissolved in dichloromethane (5 mL) and cooled in an ice/water bath. To this were added 1-(3-dimethylaminopropyl)-3-ethylcarbodiimide hydrochloride (95 mg), 1-hydroxybenzotriazole hydrate (50 mg), and N-methyl morpholine (0.1 mL) and the reaction was stirred for 1 h. The compound from PREPARATION 18 (150 mg) was then added and the mixture stirred at ambient temperature overnight before removing the solvent in vacuo. To the resulting mixture was added 1 M sodium bicarbonate and ethyl acetate; the organic layer was separated and washed with water and brine before drying with magnesium sulphate, filtering, and concentrating to a crude mixture. Silica gel chromatography using dichloromethane:methanol (95:5) eluant yielded pure product (60 mg).

¹H NMR: 7.48–6.96 (m, 6H), 3.30–1.22 (m, 30H).

LRMS m/z 630 (m+H)⁺.

$[a]_D^{25}$=+16.4° (c=1.0 mg/mL in MeOH).

EXAMPLE 18

(+)-3(R)-1-(3-Chlorobenzoyl)-3-(3,4-dichlorophenyl)3-(3-[3-(4-methanesulphonylpiperazin-1-yl)azetidin-1-yl]propyl)-piperidine

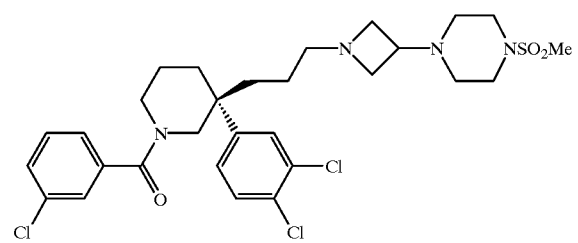

3-Chlorobenzoic acid (140 mg) was dissolved in dichloromethane (5 mL) and cooled in an ice/water bath. To this were added 1-(3-dimethylaminopropyl)-3-ethylcarbodiimide hydrochloride (95 mg), 1-hydroxybenzotriazole hydrate (50 mg), and N-methyl morpholine (0.1 mL) and the reaction was stirred for 1 h. The compound from PREPARATION 18 (150 mg) was then added and the mixture stirred at ambient temperature overnight before removing the solvent in vacuo. To the resulting mixture was added 1 M sodium bicarbonate and ethyl acetate; the organic layer was separated and washed with water and brine before drying with magnesium sulphate, filtering, and concentrating to a crude mixture. Silica gel chromatography using dichloromethane:methanol (95:5) eluant yielded the title compound.

¹H-NMR: 7.42–7.06 (m, 6H), 3.38–1.37 (m, 30H)

LRMS m/z 629 (m+H)⁺

$[a]_D^{25}$=+13.4° (c=1.0 mg/mL in MeOH)

Found: C, 55.17; H, 6.08; N, 8.70. $C_{29}H_{37}N_4O_3SCl_3$

Requires: C, 55.46, H, 5.94, N, 8.92

EXAMPLE 19

(+)-3(R)-1-Benzoyl-3-(3,4-dichlorophenyl)-3-(3-[3-piperazinoazetidin-1-yl]propyl)piperidine

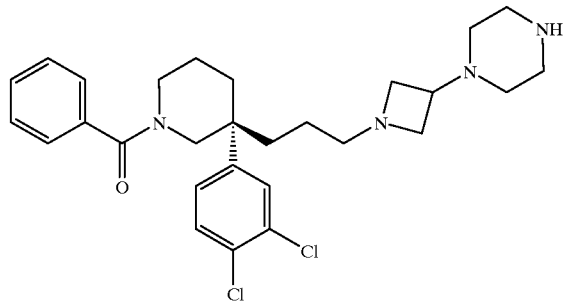

The compound of EXAMPLE 1 (14.55 g) was dissolved in trifluoroacetic acid (100 mL) and the solution stirred at room temperature under nitrogen for 1 hour. The reaction mixture was evaporated to dryness in vacuo. The residue was dissolved in ethyl acetate (1500 mL) and washed with saturated sodium bicarbonate solution, dried over sodium sulphatee and evaporated to dryness in vacuo. The residue was purified by column chromatography over silica gel (dichloromethane/methanol/ammonium hydroxide 85/15/2) to afford the title compound as a foam (9.77 g).

TLC $R_f$: 0.21 (dichloromethane/methanol/ammonium hydroxide 90/10/2 by volume).

LRMS m/z: 515 (MH⁺).

¹H NMR: 7.32 (m, 4H), 7.20 (m, 4H), 4.62 (s, 1H), 4.43 (br s, 1H), 3.45–3.09 (m, 4H), 2.91–2.60 (m, 6H), 2.38–2.00 (m, 7H), 1.82–1.08 (m, 7H), 0.92 (m, 1H).

Found: C, 62.95; H, 6.97; N, 10.52. $C_{28}H_{36}Cl_2N_4O \cdot 0.3/10CH_2Cl_2$ requires C, 62.83; H, 6.82; N, 10.36%

$[a]_D$+22.0° (c=0.10, methanol).

EXAMPLE 20

3(R)-1-Benzoyl-3-(3,4-dichlorophenyl)-3-(3-[3-(homopiperazin-1-yl)azetidin-1-yl]propyl)piperidine trifluroacetic acid salt

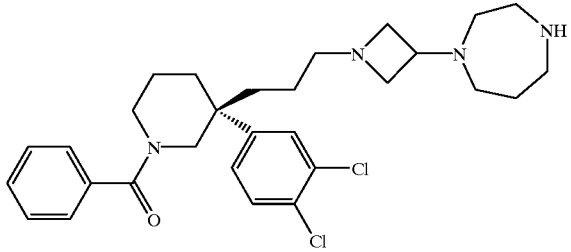

The compound from EXAMPLE 2 (300 mg) was dissolved in dichloromethane (7 mL), cooled in an ice/water bath and treated with trifluoroacetic acid (7 mL). After 2 h, the mixture was diluted with dichloromethane (50 mL) and 1 N sodium carbonate slowly until no effervesence was observed. The organic layer was separated (with difficulty) and washed with brine, dried over magnesium sulphate, and filtered to give a crude material (269 mg) which needed no further purification.

$^1$H NMR: 7.48–7.20 (m, 8H), 3.45–1.22 (m, 29H).

TLC (dichloromethane:methanol:ammonium hydroxide= 90:10:1) $R_f$=0.13.

m/z 529 (m+H)$^+$.

The following Preparations illustrate the synthesis of certain starting materials used in the preceding Examples.

PREPARATION 1

2-(3,4-Dichlorophenyl)-5-hexenenitrile

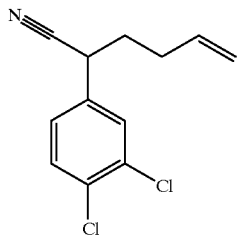

To a solution of sodium hydride (14.8 g, 60% dispersion in mineral oil) in dimethylformamide (DMF, 150 ml) at 0° C. under nitrogen was added a solution of 3,4-dichlorophenylacetonitrile (68.9 g, 1 mol. equivalent) in DMF (300 ml) and the mixture was stirred for 3 hours. A solution of 4-bromobut-1-ene (50 g, 1 mol. eq.) in DMF (100 ml) was then added, and the mixture was stirred at room temperature for one hour, then heated to 60° C. for 5 hours. The reaction mixture was cooled and water (1 liter) was added. The mixture was then extracted with ethyl acetate (2×500 ml). The combined organic extracts were then washed with water (2×1 liter), dried over MgSO$_4$ and the solvent was removed under reduced pressure. The residue was then purified by column chromatography using silica gel, eluting with a solvent gradient of ethyl acetate-:hexane (1:19 to 1:6, by volume) to give the title compound (51.5 g).

TLC (hexane:ethyl acetate 6:1) $R_f$=0.47.

$^1$H NMR: 1.85–2.1 (m,2H); 2.2–2.3 (m,2H); 3.75–3.8 (m, 1H); 5.05–5.1 (m,2H); 5.7–5.8 (m,1H); 7.15–7.2 (m, 1H); 7.4–7.45 (m,2H).

PREPARATION 2

4-Cyano-4-(3,4-dichlorophenyl)oct-7-enoic acid

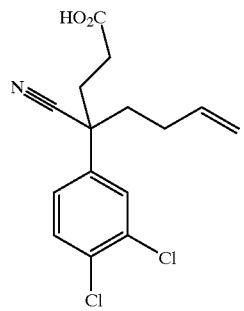

To a solution of the compound of Preparation 1 (50.5 g, 210.4 mmol) in dioxan (150 ml) at 0° C. under nitrogen was added potassium tert-butoxide (1.5 g, 0.06 mol.eq.) and ethyl acrylate (25.4 ml, 1.11 mol.eq.), and the mixture was stirred for 1 hour. Aqueous sodium hydroxide solution (2N, 150 ml) was then added and the mixture was stirred at room temperature for 70 minutes. Methyl tert-butyl ether (300 ml) was then added, and the mixture was acidified to pH 1 using aqueous 2N hydrochloric acid solution, the solution was then extracted with methyl tert-butyl ether (2×300 ml) and the combined organics were then dried over MgSO$_4$ and filtered, removal of the solvent in vacuo gave the title compound (68.12 g).

$^1$H NMR: 1.8–2.6 (m,9H), 4.9–5.0 (m,2H), 5.65–5.75 (M,1H), 7.2–7.25 (m,1H), 7.45–7.5 (m,2H).

PREPARATION 3

(+)-4S-4-Cyano-4-(3,4-dichlorophenyl)oct-7-enoic acid

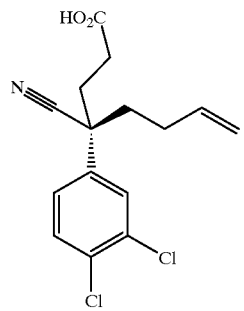

Part a)

A mixture of the compound of PREPARATION 2 (247 g) in acetone (247 ml) and S-(−)-1-(1-naphthyl)ethylamine (68.8 g) was heated to 50° C. and warm hexane (1200 ml) added until cloudiness appeared. The mixture was warmed back to 50° C. and sufficient additional hexane (50 ml) added to induce cloudiness again. The resulting cloudy solution was stirred at room temperature for 18 hours. The sticky precipitate was collected by filtration and washed with hexane (3×200 ml) and acetone/hexane (200 ml; 10% by volume). The solid was dried at 50° C. to afford the 1-naphthyl)ethylamine salt of the title compound, 108.7 g. This material was stirred in acetone (300 ml) and the small amount of insoluble material removed by filtration. The filtrate was stirred at room temperature and hexane (1200 ml) added to the cloud point. Precipitation occured withing 5 minutes and, after stirring at room temperature for 1 hour, the solid precipitate was collected by filtration and dried (54.1 g). The process was repeated with 210.3 g of the compound of PREPARATION 2 and (S)-(−)-1-(1-naphthyl) ethylamine (58.7 g) to afford a solid which was combined with the 54.1 g of product obtained in the first run to give a total yield of 135.2 g.

Part b)

The salt from part a) was stirred in dichloromethane (1000 ml) and water (1000 ml) and basified with 40% sodium hydroxide solution. The mixture was stirred for 30 minutes to afford a stable emulsion which was treated with solid sodium chloride. After a further period of stirring (15 minutes) the layers were separated and the aqueous solution was diluted with water (1000 ml) and washed with further dichloromethane (1000 ml). The combined organic washes were washed with saturated brine solution and evaporated to dryness the recover the chiral resolving agent (45 g). The aqueous phase was stirred with dichloromethane (1500 ml) and acidified to pH<0.5 with concentrated hydrochloric acid and the resulting mixture was stirred for a further 30 minutes. The layers were separated and the aqueous layer extracted with dichloromethane (500 ml). The combined organic extracts were washed with water, dried over sodium sulphate and evaporated to dryness in vacuo to afford the title compound as a white solid, (69.8 g).

TLC $R_f$: 0.19 (dichloromethane/methanol/ammonium hydroxide 85/15/2 by volume).

m/z: 329 ($MNH_4^+$).

$^1$H NMR: 7.43 (m, 2H), 7.21 (m, 1H), 5.70 (m, 1H), 4.97 (m, 2H), 2.60–1.80 (m, 9H).

$[a]_D$−11.4° (c=0.45, methanol)

PREPARATION 4

(−)-4R-4-Cyano-4-(3,4-dichlorophenyl)-7-hydroxyheptanoic acid

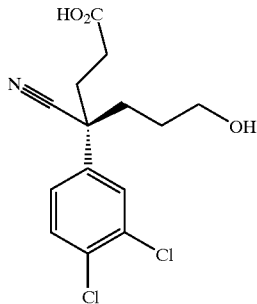

Ozone in a stream of oxygen was bubbled through a solution of the compound of Preparation 3 (15.6 g) in ethanol (400 mL) at −78° C. for 1 hour. The cooling was removed and the resulting blue/green solution was purged with nitrogen for 1 hour to remove excess ozone. The solution was then cooled in an ice-bath and sodium borohydride (9.45 g) was added portionwise and the resulting mixture was stirred at room temperature for 18 hours. The solution was cooled in an ice-bath and the solution acidified to pH 2 by the cautious addition of 5N hydrochloric acid. The partially worked up reaction was combined with the partially worked up material from an identical preparation and diluted with water (300 mL). The resulting solution was extracted into dichloromethane (3×1000 mL). The combined organic extracts were dried over magnesium sulphate and evaporated in vacuo to afford the title compound as a foam (30.0 g) which was used without any further purification.

TLC $R_f$: 0.11 (dichloromethane/methanol/ammonium hydroxide 80/20/3 by volume).

m/z: 333 ($MNH_4^+$).

$^1$H NMR: 7.48 (m, 2H), 7.24 (m, 1H), 4.40 (broad s, 2H), 3.62 (t, 2H), 2.62–1.97 (m, 6H), 1.72 (m, 1H), 1.38 (m, 1H).

$[a]_D$−10.2° (c=0.10, methanol).

PREPARATION 5

(+)-3(R)-3-(3-Acetyloxypropyl)-3-(3,4-dichlorophenyl)glutarimide

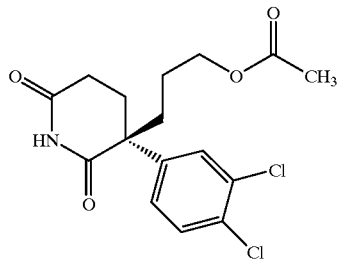

Concentrated sulphuric acid (3 mL) was added to a solution of the compound of PREPARATION 4 (29.7 g) in glacial acetic acid (400 mL), and the mixture heated under reflux for 6 hours. The reaction mixture was cooled to room temperature and allowed to stand for 18 hours. Evaporation of the volatiles in vacuo afforded a residue which was dissolved in dichloromethane (1000 mL) and washed with saturated sodium hydrogen carbonate solution and saturated brine. The organic solution was dried over sodium sulphate and evaporated to dryness in vacuo to afford the title compound as an off white solid, (31.48 g) which was used without further purification.

TLC $R_f$: 0.55 (dichloromethane/methanol 95/5 by volume).

m/z: 375 ($MNH_4^+$)

$^1$H NMR: 7.85 (broad s, 1H), 7.44 (d, 1H, 7.34 (s, 1H), 7.09 (d, 1H), 3.98 (t, 2H), 2.62 (m, 1H), 2.34 (m, 2H), 2.21 (m, 1H), 1.95 (m, 5H), 1.57 (m, 2H).

$[a]_D$+108.2° (c=0.118, methanol).

PREPARATION 6

(−)-3(S)-3-(3,4-Dichlorophenyl)-3-(3-hydroxyropyl)piperidine

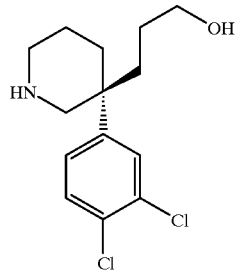

Borane dimethylsulphide complex (83 mL) was added dropwise over 10 minutes to a solution of the compound of PREPARATION 5 (31.27 g) in dry tetrahydrofuran (450 mL) at 0° C. The mixture was allowed to warm to room temperature over 30 minutes and then to reflux over an hour. After 2 hours at reflux the solution was cooled in an ice-bath and methanolic hydrogen chloride (300 mL of an approximately 1.75N solution) was added dropwise with caution over a period of 1 hour. The strongly acidic solution was allowed to warm to room temperature and stirred at this temperature overnight. The solution was evaporated to dryness in vacuo and the residue was partitioned between water (500 mL) and diethyl ether (500 mL). The aqueous solution was washed with further diethyl ether (500 mL) and the combined organics discarded. The aqueous solution was basified with ammonium hydroxide (s.g. 0.880) and extracted into diethyl ether (2×750 mL). The combined extracts were dried over sodium sulphate and evaporated to dryness to afford the title compound as a gum, 25.2 g which was used without further purification. A small quantity (650 mg) was purified by column chromatography over silica gel (dichloromethane/methanol/ammonium hydroxide) to afford a pure sample of the title compound, (546 mg).

TLC $R_f$: 0.34 (dichloromethane/methanol/ammonium hydroxide 90/10/2 by volume).

LRMS m/z: 288 (MH$^+$).

$^1$H NMR: 7.37 (m, 2H), 7.12 (d, 1H), 3.45 (t, 2H), 3.18 (d, 1H), 2.80 (m, 3H), 2.01 (m, 1H), 1.70 (m, 1H), 1.59 (m, 5H), 1.42 (m, 1H), 1.15 (m, 2H).

$[a]_D$ −3.7° (c=0.107, methanol)

PREPARATION 7

(+)-3(S)-1-Benzoyl-3-(3,4-dichlorophenyl)-3-(3-hydroxypropyl)piperidine

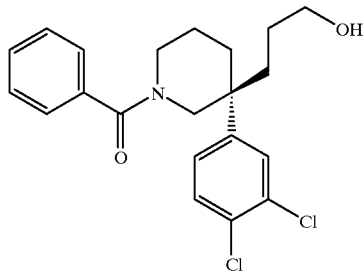

To an ice-cold solution of the compound of PREPARATION 6 (15.44 g) and triethylamine (13.01 g) in dry dichloromethane (300 mL) was added benzoyl chloride (16.57 g) slowly over about 10 minutes. The resulting mixture was allowed to warm to room temperature and was stirred for 24 hours. The reaction mixture was evaporated to dryness in vacuo and the residue was dissolved in ethanol (300 mL) and dichloromethane (100 mL). To this solution was added sodium hydroxide (155 mL of 2N aqueous solution) and the resulting mixture was stirred at room temperature for 5 hours. The solution was cooled in an ice-bath and acidified to pH6 using 6N hydrochloric acid and then evaporated to low volume. The mixture was extracted with ethyl acetate (2×300 mL) and the combined extracted dried over sodium sulphate and evaporated to dryness in vacuo. The residue was purified by column chromatography over silica gel (dichloromethane/methanol/ammonium hydroxide 95/5/0.5 by volume) to afford the title compound as a white foam (19.90 g).

TLC $R_f$: 0.32 (dichloromethane/methanol/ammonium hydroxide 95/5/0.5 by volume)

m/z: 393 (MH$^+$)

$[a]_D$ +35.1° (c=0.13, methanol)

PREPARATION 8

(+)-3(S)-1-Benzoyl-3-(3,4-dichlorophenyl)-3-(3-methanesulphonyloxypropyl)piperidine

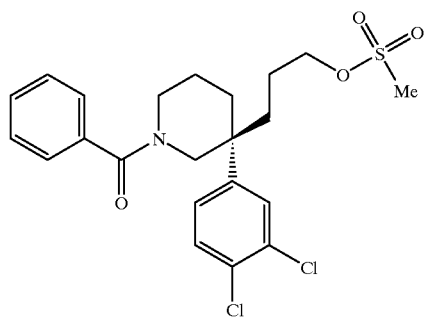

Methanesulphonyl chloride (4.63 mL) was added over a period of 10 minutes to an ice-cold solution of the compound of PREPARATION 7 (19.57 g) and triethylamine (9.74 mL) under nitrogen. The reaction mixture was stirred at 0° C. for 30 minutes and then warmed to room temperature. The reaction was diluted with dichloromethane (150 mL) and washed successively with water, 1N aqueous citric acid solution and saturated aqueous sodium bicarbonate solution. The organic phase was dried over sodium sulphate and evaporated to dryness in vacuo to afford the title compound as a foam (23.06 g).

TLC $R_f$: 0.61 silica, dichloromethane/methanol 95/5 by volume.

LRMS m/z: 471 (MH$^+$).

$^1$H NMR: 7.39 (m, 5H), 7.24 (m, 3H), 4.35 (m, 1H), 4.09 (m, 2H), 3.58 (d, 1H), 3.40 (m, 2H), 2.95 (s, 3H), 2.12 (m, 1H), 1.93–1.28 (m, 7H).

$[a]_D$ +34.2° (c=0.168, methanol)

PREPARATION 9

3-(4-tert-Butoxycarbonylpiperazin-1-yl)-1-diphenylmethylazetidine

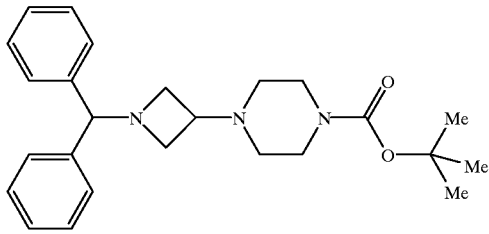

A mixture of N-tert-butoxycarbonylpiperazine (14.08 g), potassium carbonate (26.1 g), and 1-diphenylmethyl-3-methanesulphonyloxyazetidine (WO 96/05193) (20 g) in dry acetonitrile (600 mL) was heated under reflux for 32 hours. The reaction mixture was cooled to room temperature, diluted with ethyl acetate and washed with water and brine. The organic phase was dried over sodium sulphate and evaporated to dryness in vacuo. The residue was purified by column chromatography over silica (dichloromethane/methanol 97/3 by volume) to afford the title compound as a solid (22.53 g).

TLC $R_f$: 0.17 (dichloromethane/methanol 98/2 by volume).

LRMS m/z: 408(MH$^+$).

PREPARATION 10

3-(4-tert-Butoxycarbonylpiperazin-1-yl)azetidine

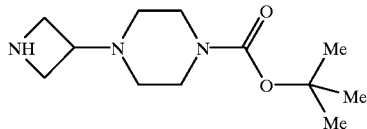

1-Chloroethyl chloroformate (6.88 mL) was added dropwise to an ice-cold solution of the compound of PREPARATION 9 (22 g) in dry dichloromethane (100 mL). The resulting mixture was stirred at room temperature for 3 hours, before the volatiles were evaporated in vacuo. To the residue was added powdered potassium carbonate (13.2 g) and methanol (125 mL) and the mixture was heated under reflux for 2 hours. The cooled reaction mixture was filtered through SOLKAFLOC™ filter aid and the filtrate was evaporated to dryness in vacuo. The residue was purified by column chromatography over silica gel (dichloromethane/methanol/ammonium hydroxide 80/20/3) to afford the title compound (14 g). TLC $R_f$: 0.14 (dichloromethane/methano/ammonium hydroxide 90/10/2 by volume).

LRMS m/z: 242 (MH$^+$).

PREPARATION 11

1-Diphenylmethyl-3-(4-tert-butoxycarbonylhomopiperazin-1-yl)azetidine

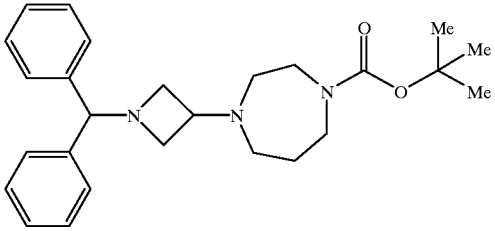

To a solution of 1-diphenylmethyl-3-methanesulphonyloxyazetidine (WO 96/05193) (25 g) in acetonitrile (800 mL) were added the compound of PREPARATION 24 (19 g) and potassium carbonate (33 g). The reaction mixture was heated to reflux for 12 h, then cooled to room temperature. Water was added to the resulting slurry, and the mixture extracted three times with ethyl acetate. The combined organics were washed with brine, dried over magnesium sulphate, filtered and dried in vacuo to yield crude product. Chromatography on silica gel eluting with dichloromethane:methanol (95:5) yielded the title compound (24.7 g).

$^1$H NMR: 7.41–7.14 (m, 10H), 4.39 (s, 1H), 3.41 (m, 6H), 3.15 (m, 1H), 2.82 (m, 2H), 2.38 (m, 4H), 1.78 (m, 2H), 1.45 (s, 9H).

LRMS m/z 422 (m+H)$^+$.

PREPARATION 12

3-(4-tert-Butoxycarbonylhomopiperazin-1-yl)azetidine

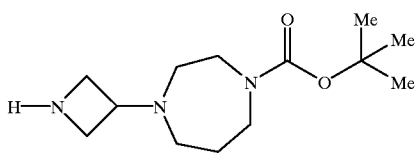

The compound from PREPARATION 11 (1.0 g) was dissolved in ethanol (75 mL) and mixed with palladium hydroxide (Pearlman's catalyst, 200 mg), then subjected to hydrogen gas at 345 kPa (50 p.s.i.) for 16 h. The catalyst was removed by filtration and the filtrate evaporated to dryness. Chromatography on silica gel with dichloromethane:methanol:ammonium hydroxide (90:10:2) as eluant yielded the title product.

$^1$H NMR: 3.55–3.38 (m, 10H), 2.40 (m, 4H), 1.82 (m, 2H), 1.46 (s, 9H).

m/z 256 (m+H)$^+$.

PREPARATION 13

(+)-3(R)-1-Benzoyl-3-(3,4-dichlorophenyl)-3-(3-[3-piperazinoazetidin-1-yl]propyl)piperidine

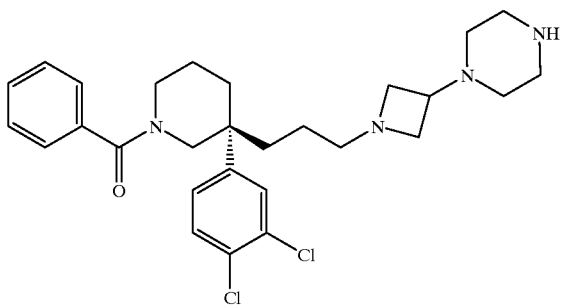

The compound of EXAMPLE 1 (14.55 g) was dissolved in trifluoroacetic acid (100 mL) and the solution stirred at room temperature under nitrogen for 1 hour. The reaction mixture was evaporated to dryness in vacuo. The residue was dissolved in ethyl acetate (1500 mL) and washed with saturated sodium bicarbonate solution, dried over sodium sulphatee and evaporated to dryness in vacuo. The residue was purified by column chromatography over silica gel (dichloromethane/methanol/ammonium hydroxide 85/15/2) to afford the title compound as a foam, 9.77 g.

TLC $R_f$: 0.21 (dichloromethane/methanol/ammonium hydroxide 90/10/2 by volume).

LRMS m/z: 515 (MH$^+$).

$^1$H NMR: 7.32 (m, 4H), 7.20 (m, 4H), 4.62 (s, 1H), 4.43 (br s, 1H), 3.45–3.09 (m, 4H), 2.91–2.60 (m, 6H), 2.38–2.00 (m, 7H), 1.82–1.08 (m, 7H), 0.92 (m, 1H).

Found: C, 62.95; H, 6.97; N, 10.52. $C_{28}H_{36}Cl_2N_4O.3/10CH_2Cl_2$ requires C, 62.83; H, 6.82; N, 10.36%

$[a]_D$ +22.0° (c=0.10, methanol).

PREPARATION 14

3(R)-1-Benzoyl-3-(3,4-dichlorophenyl)-3-(3-[3-(homopiperazin-1-yl)azetidin-1-yl]propyl)piperidine trifluroacetic acid salt

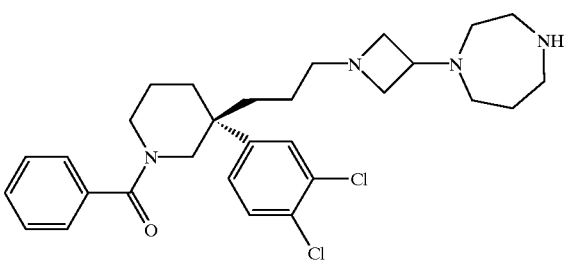

The compound from EXAMPLE 2 (300 mg) was dissolved in dichloromethane (7 mL), cooled in an ice/water bath and treated with trifluoroacetic acid (7 mL). After 2 h, the mixture was diluted with dichloromethane (50 mL) and 1 N sodium carbonate slowly until no effervesence was observed. The organic layer was separated (with difficulty) and washed with brine, dried over magnesium sulphate, and filtered to give a crude material (269 mg) which needed no further purification.

$^1$H NMR: 7.48–7.20 (m, 8H), 3.45–1.22 (m, 29H).

TLC (dichloromethane:methanol:ammonium hydroxide= 90:10:1) $R_f$=0.13.

LRMS m/z 529 (m+H)$^+$.

PREPARATION 15

3(S)-1-tert-Butoxycarbonyl-3-(3,4-dichlorophenyl)-3-(3-hydroxypropyl)piperidine

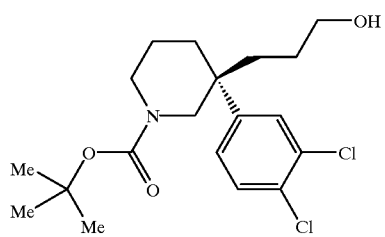

The compound from PREPARATION 6 (5.0 g) and tert-butoxycarbonyl anhydride were dissolved in dichloromethane (50 mL) and stirred at ambient temperature overnight. The solution was washed with aqueous sodium bicarbonate and brine, dried over magnesium sulphate, filtered, and evacuated to dryness to give the product (5.59 g).

$^1$H NMR: 7.43 (s, 1H), 7.39 (d, J=8Hz, 1H), 7.18 (d, J=8Hz, 1H), 3.98 (m, 1H), 3.78–3.02 (m, 6H), 2.03 (m, 1H), 1.80–1.03 (m, 17H).

m/z 389 (m+H)$^+$.

PREPARATION 16

3(S)-1-tert-Butoxycarbonyl-3-(3,4-dichlorophenyl)-3-(3-methanesulphonyloxypropyl)piperidine

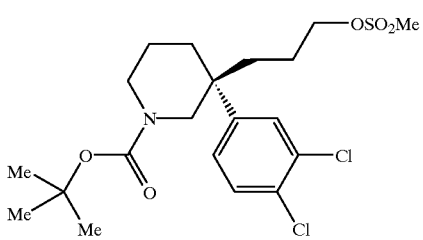

Methanesulphonyl chloride (1.22 mL) was added dropwise to a solution of the compound from PREPARATION 15 (5.58 g) and triethylamine (3.0 mL) in dichloromethane (50 mL) while cooling in an ice bath. The mixture was then allowed to warm to ambient temperature for 1.5 hours before quenching with with aqueous sodium bicarbonate. The extracted organic layer was washed with brine, dried over magnesium sulphate, filtered, and evacuated to dryness to give the product (6.37 g).

$^1$H NMR: 7.41 (m, 2H), 7.19 (m, 1H), 4.04 (t, J=7Hz, 2H), 4.02 (m, 1H), 3.70–3.10 (m, 3H), 2.93 (s, 3H), 2.03 (m, 1H), 1.80–1.22 (m, 12H).

LRMS m/z 270 ([m−HOSO$_2$Me]+H)$^+$.

PREPARATION 17

3(R)-1-tert-Butoxycarbonyl-3-(3,4-dichlorophenyl)-3-(3-[3-(4-methanesulphonylpiperazin-1-yl)azetidin-1-yl]propyl)piperidine

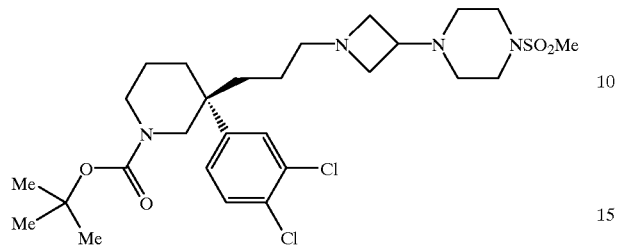

The compound from PREPARATION 16 (1.0 g) was mixed with the compound from PREPARATION 22 (603 mg) and potassium hydrogen carbonate (643 mg) in acetonitrile (30 mL) and the mixture was heated to reflux overnight. The reaction mixture was cooled to ambient temperature and partitioned between ethyl acetate (50 mL) and water (25 mL). The organic layer was then washed with brine, dried over magnesium sulphate, filtered, and evaporated in vacuo to yield a crude mixture. Purification on silica gel with dichloromethane:methanol:ammonium hydroxide (98:2:1) yielded the desired compound (1.18 g).

$^1$H NMR: 7.42–7.34 (m, 2H), 7.12 (m, 1H), 4.02 (m, 1H), 3.71–1.90 (m, 22H), 1.75–0.78 (m, 17H).

m/z 591 (m+H)$^+$.

PREPARATION 18

3(S)-3-(3,4-dichlorophenyl)-3-(3-[3-(4-methanesulphonylpiperazin-1-yl)azetidin-1-yl]propyl)piperidine

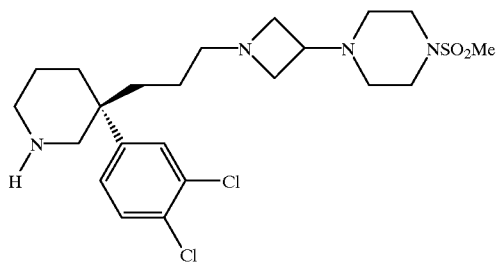

The compound from PREPARATION 17 (606 mg) was dissolved in dichloromethane (2 mL) and cooled in an ice water bath before trifluoroacetic acid (2 mL) was added. After 1 h, toluene (10 mL) was added followed by solvent evaporation in vacuo. To the residue was added 0.2 N sodium hydroxide (50 mL), and the mixture was extracted repeatedly with dichloromethane. The combined organic phases were dried over magnesium sulphate, filtered, and evaporated to give a white solid (376 mg).

$^1$H NMR: 7.38 (m, 2H), 7.12 (m, 1H), 3.31–1.82 (m, 22H), 1.8–1.38 (m, 6H), 0.93 (m, 2H).

m/z 491 (m+H)$^+$.

PREPARATION 19

1-Diphenylmethyl-3-(N-methyl benzenesulphonamido)azetidine

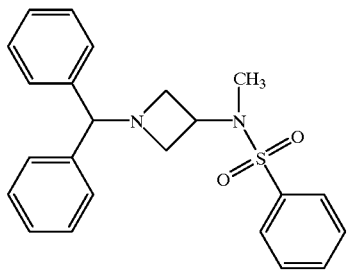

To a solution of 1-diphenylmethyl-3-methanesulphonyloxyazetidine (WO 96/05193) (1.4 g) in dioxane (25 mL) were added N-methyl benzenesulphonamide (1.2 g) and caesium carbonate (2.6 g). The reaction mixture was heated to reflux for 3 h, then cooled to room temperature. Water (20 mL) was added to the resulting slurry, and the mixture was extracted with ethyl acetate (3×25 mL). The combined organics were washed with brine, dried over magnesium sulphate, filtered and dried in vacuo to yield crude product. Chromatography on silica gel eluting with ethyl acetate:hexanes (2:3 by volume) yielded the title compound as a white foam (1.31 g).

$^1$H NMR: 7.68 (d, J=8 Hz, 2H), 7.54 (t, J=8 Hz, 1H), 7.46 (t, J=8 Hz, 2H), 7.32 (d, J=7 Hz, 4H), 7.22 (t, J=7 Hz, 4H), 7.14 (t, J=7Hz, 2H), 4.27 (s, 1H), 3.92 (quintet, J=7Hz, 1H), 3.33 (t, J=7 Hz, 2H), 2.99 (t, J=7 Hz, 2H), 2.66 (s, 3H).

m/z 393 (m+H)$^+$

PREPARATION 20

3-(N-Methyl benzenesulphonamido)azetidine

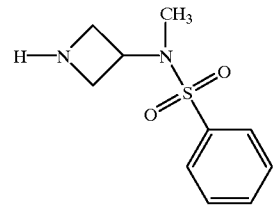

The compound from PREPARATION 19 (1.3 g) was dissolved in ethanol (30 mL) and mixed with palladium hydroxide (Pearlman's catalyst, 600 mg), then subjected to hydrogen gas at 345 kPa (50 p.s.i.) for 24 h. The catalyst was removed by filtration and the filtrate evaporated to dryness. Chromatography on silica gel with dichloromethane:methanol:ammonium hydroxide (93:7:1) as eluant yielded the title compound.

$^1$H NMR: 7.70 (d, J=7Hz, 2H), 7.61 (t, J=7Hz, 1H), 7.53 (t, J=7Hz, 2H), 4.60 (m, 1H), 4.06 (dd, J=11 and 8Hz, 2H), 3.99 (dd, J=11 and 8Hz, 2H), 3.45 (s, 1H), 2.76 (s, 3H).

m/z 227 (m+H)$^+$.

PREPARATION 21

1-Diphenylmethyl-3-(N-phenyl methanesulphonamido)azetidine

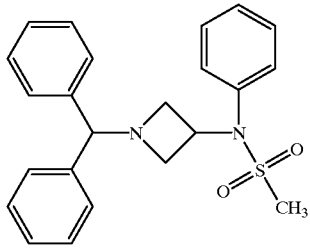

To a solution 1-diphenylmethyl-3-methanesulphonyloxyazetidine (WO 96/05193) (1.2 g) in dioxane (15 mL) was added N-phenyl methanesulphonamide (1.0 g, 5.85 mmol) and caesium carbonate (2.0 g, 6.1 mmol). The reaction mixture was heated to reflux for 2 h, then cooled to room temperature. Water (20 mL) was added to the resulting slurry, and the mixture was extracted with magnesium sulphate, filtered and dried in vacuo to yield crude product. Rescrystallization from ethyl acetate:hexanes (4:1) gave 964 mg of a white solid.

$^1$H NMR: 7.38–7.09 (m, 15H), 4.55 (m, 1H), 4.17 (s, 1H), 3.47 (dd, J=7 and 3Hz, 2H), 2.81 (dd, J=7 and 3Hz, 2H), 2.76 (s, 3H).

m/z 393 (m+H)$^+$.

PREPARATION 22

3-(N-Phenyl methanesulphonamido)azetidine

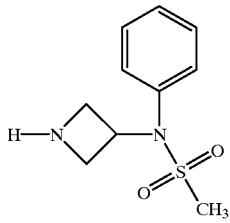

The compound from PREPARATION 21 (890 mg) was dissolved in ethanol (30 mL) and mixed with palladium hydroxide (Pearlman's catalyst, 800 mg), then subjected to hydrogen gas at 345 kPa (50 p.s.i.) for 48 h. The catalyst was removed by filtration and the filtrate was evaporated to dryness. Chromatography on silica gel with dichloromethane:methanol:ammonium hydroxide (93:7:1) as eluant yielded pure product.

$^1$H NMR: 7.41–7.30 (m, 3H), 7.21 (m, 2H), 4.84 (m, 1H), 3.59 (m, 4H), 2.80 (s, 3H), 1.69 (br s, 1H)

m/z 227 (m+H)$^+$

PREPARATION 22

1-Diphenylmethyl-3-(4-methanesulphonylpiperazinyl)azetidine

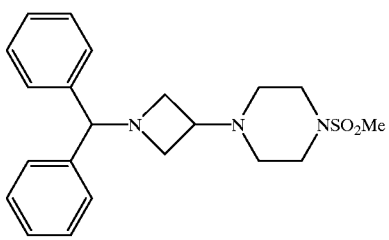

To a solution 1-diphenylmethyl-3-methanesulphonyloxyazetidine (WO 96/05193) (7.73 g) in acetonitrile (250 mL) was added methanesulphonylpiperazine (4.8 g). The reaction mixture was heated to reflux overnight, then cooled to room temperature and concentrated to a foam. Purification on silica gel with dichloromethane:methanol:ammonium hydroxide (95:5:0.5) as eluant yielded pure product (5.97 g).

TLC (dichloromethane:methanol:ammonium hydroxide 90:10:1) R$_f$=0.44 m/z 386 (m+H)$^+$

PREPARATION 23

3-(4-Methanesulphonylpiperazine)azetidine

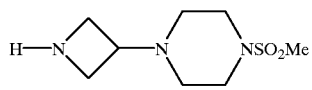

The compound from PREPARATION 22 (2.77 g) was dissolved in anhydrous dichloromethane (40 mL), cooled in an ice bath, and treated with 1-chloroethyl chloroformate (2.06 g). The solution was allowed to warm to ambient temperature and was stirred for 3 h before removing the solvent in vacuo. To the residue was added methanol (40 mL) and the solution was heated to reflux for 1 h. After cooling to ambient temperature and stirring overnight, the resulting precipitate was collected by filtration.

$^1$H NMR:: 4.32 (m, 2H), 4.11 (m, 1H), 3.99 (m, 2H), 3.38 (m, 4H), 2.95 (s, 3H), 2.21 (m, 4H)

m/z 221 (m+H)$^+$

PREPARATION 24

4-tert-Butoxycarbonylhomopiperazine

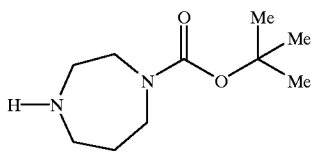

tert-Butoxycarbonyl anhydride (195 g) was dissolved in dichloromethane (350 mL) and added dropwise to a solution of homopiperazine (100 g) and triethylamine (210 mg) in dichloromethane (500 mL) while cooling in an ice/water bath. The mixture was stirred overnight, allowing to warm to ambient temperature. After removing the solvent in vacuo, the crude mixture was partitioned between 2 N citric acid (aqueous) and diethyl ether. The aqueous layer was washed with diethyl ether, then basified with 2 N sodium hydroxide and extracted repeatedly with dichloromethane. The combined dichloromethane layers were combined, dried over magnesium sulphate, filtered, and evaporated to dryness to yield a yellow oil (170 g).

TLC (dichloromethane:methanol:ammonium hydroxide= 90:10:1) $R_f$=0.43 m/z 201 (m+H)$^+$.

PREPARATION 25

3-morpholinoazetidine dihydrochloride

A mixture of 1-diphenylmethyl-3-morpholinoazetidine (prepared in an analogous manner to the compound of preparation 22 above) (18.6 g), palladium hydroxide (2 g), ethanol (200 ml) and 1N aqueous hydrochloric acid solution (52 ml) was stirred under an atmosphere of hydrogen at 345 kPa (50 p.s.i.) for 3 days. The catalyst was then removed by filtration and the filtrate evaporated to dryness. Addition of dichloromethane (100 ml) to the residue and trituration gave a solid which was recrystallised from methanol to give the title compound (10.2 g).

m/z 179 (m+H)$^+$.

PHARMACOLOGICAL DATA

The data below illustrates the in vitro affinity of substances of the invention for the guinea pig cortex $NK_3$ receptor, which assays were carried out according to the method mentioned earlier on page 15.

| Example | pIC$_{50}$ |
|---|---|
| 3 | 8.8 |
| 13 | 7.95 |
| 17 | 8.4 |

What is claimed is:

1. A compound of the formula (I):

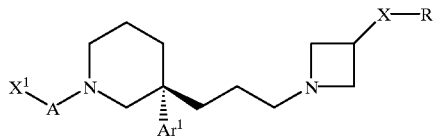

and pharmaceutically-acceptable salts thereof, wherein

A is CO, SO$_2$ or CH$_2$;

Ar$^1$ is phenyl optionally substituted by one or more substituents independently selected from halogen, C$_{1-6}$ alkoxy optionally substituted by one or more halogen, and C$_{1-6}$ alkyl optionally substituted by one or more halogen;

X$^1$ is C$_{3-7}$ cycloalkyl, aryl or C$_{1-6}$ alkyl,
said C$_{1-6}$ alkyl being optionally substituted by fluoro, CO$_2$H, CO$_2$(C$_{1-4}$alkyl), C$_{3-7}$ cycloalkyl, adamantyl, aryl or het,
and said C$_{3-7}$ cycloalkyl being optionally substituted by 1 or 2 substituents each independently selected from C$_{1-4}$ alkyl, C$_{3-7}$ cycloalkyl, C$_{1-4}$ alkoxy, OH, F, fluoro(C$_{1-4}$ alkyl) and fluoro(C$_{1-4}$ alkoxy);

X is a direct link or NR$^1$;

R is SO$_2$aryl, SO$_2$(C$_{1-6}$ alkyl optionally substituted by one or more halogen),

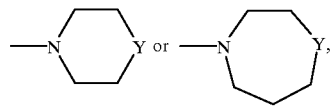

R$^1$ is H, C$_{1-6}$ alkyl optionally substituted by one or more halogen,
or R$^1$ is phenyl optionally substituted by one or more substituents independently selected from halogen, C$_{1-6}$ alkoxy optionally substituted by one or more halogen, or C$_{1-6}$ alkyl optionally substituted by one or more halogen;

Y is O, NCO(C$_{1-6}$ alkyl optionally substituted by one or more halogen), NCO$_2$(C$_{1-6}$ alkyl optionally substituted by one or more halogen), NSO$_2$(C$_{1-6}$ alkyl optionally substituted by one or more halogen), NCOaryl, NCO$_2$aryl, NSO$_2$aryl, NSO$_2$(C$_{1-6}$ alkyl optionally substituted by one or more halogen), CH$_2$, CHF, CF$_2$, NH, NCH$_2$aryl, N(C$_{1-6}$ alkyl optionally substituted by one or more halogen), or NCH$_2$(C$_{3-7}$ cycloalkyl);

with the proviso that X is not NR$^1$ when R is

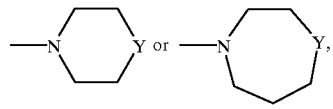

wherein "aryl" used in all the above definitions represents phenyl or naphthyl optionally substituted with one or more substituents independently selected from halogen, C$_{1-6}$ alkoxy optionally substituted by one or more halogen, or C$_{1-6}$ alkyl optionally substituted by one or more halogen;

and "het" used in the definition of X$^1$ means thienyl or a 5- or 6-membered ring heteroaryl group containing either 1 or 2 nitrogen heteroatoms or 1 nitrogen heteroatom and one oxygen or sulphur heteroatom, each optionally substituted by 1 or 2 substituents each independently selected from C$_{1-4}$ alkyl, C$_{1-4}$ alkoxy, halogen, fluoro(C$_{1-4}$ alkyl) and fluoro(C$_{1-4}$ alkoxy).

2. A compound or salt according to claim 1 wherein A is CO or SO$_2$.

3. A compound or salt according to claim 1 wherein Ar$^1$ is phenyl optionally substituted by one or more halogen atoms.

4. A compound or salt according to claim 1 wherein X$^1$ is aryl or C$_{1-6}$ alkyl, said C$_{1-6}$ alkyl being optionally substituted by fluoro, CO$_2$H, CO$_2$(C$_{1-4}$) alkyl, C$_{3-7}$ cycloalkyl, adamantyl, aryl or het,
and said C$_{3-7}$ cycloalkyl being optionally substituted by 1 or 2 substituents each independently selected from C$_{1-4}$ alkyl, C$_{3-7}$ cycloalkyl, C$_{1-4}$ alkoxy, OH, F, fluoro(C$_{1-4}$ alkyl) and fluoro(C$_{1-4}$ alkoxy).

5. A compound or salt according to claim 1 wherein X is a direct link or NR$^1$, where R$^1$ is C$_{1-6}$ alkyl optionally substituted by one or more halogen, or R$^1$ is phenyl optionally substituted by one or more halogen substituents.

6. A compound or salt according to claim 1 wherein R is SO$_2$aryl, SO$_2$(C$_{1-6}$ alkyl optionally substituted by one or more halogen),

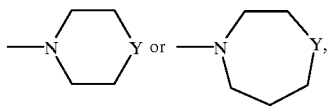

where Y is O, NCO(C$_{1-6}$ alkyl optionally substituted by one or more halogen), NCO$_2$(C$_{1-6}$ alkyl optionally substituted by one or more halogen), NSO$_2$(C$_{1-6}$ alkyl optionally substituted by one or more halogen), NCOaryl, CH$_2$, CHF, CF$_2$, NH, NCH$_2$aryl, N(C$_{1-6}$ alkyl optionally substituted by one or more halogen), or NCH$_2$(C$_{3-7}$ cycloalkyl).

7. A compound or salt according to claim 1 wherein A is CO.

8. A compound or salt according to claim 1 wherein Ar$^1$ is phenyl optionally substituted by up to two halogen atoms.

9. A compound or salt according to claim 1 wherein X$^1$ is C$_{1-6}$ alkyl substituted by C$_{3-7}$ cycloalkyl,
said C$_{3-7}$ cycloalkyl being optionally substituted by 1 or 2 substituents each independently selected from C$_{1-4}$ alkyl, C$_{3-7}$ cycloalkyl, C$_{1-4}$ alkoxy, OH, F, fluoro(C$_{1-4}$ alkyl) and fluoro(C$_{1-4}$ alkoxy),
or X$^1$ is phenyl optionally substituted by one or more substituents independently selected from halogen and C$_{1-6}$ alkyl optionally substituted by one or more halogen.

10. A compound or salt according to claim 1 wherein X is a direct link, N-methyl or N-phenyl.

11. A compound or salt according to claim 1 wherein R is SO$_2$(phenyl optionally substituted with one or more substituents independently selected from halogen, C$_{1-6}$ alkoxy optionally substituted by one or more halogen, or C$_{1-6}$ alkyl optionally substituted by one or more halogen), SO$_2$(C$_{1-3}$ alkyl optionally substituted by one or more halogen),

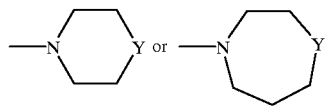

where Y is O, NCO(C$_{1-6}$ alkyl), NCO$_2$(C$_{1-6}$ alkyl), NSO$_2$ (C$_{1-6}$ alkyl optionally substituted by one or more halogen), NCO(phenyl optionally substituted with one or more substituents independently selected from halogen, C$_{1-6}$ alkoxy optionally substituted by one or more halogen, or C$_{1-6}$ alkyl optionally substituted by one or more halogen), CHF, CF$_2$, NH, NCH$_2$(phenyl optionally substituted with one or more substituents independently selected from halogen, C$_{1-6}$ alkoxy optionally substituted by one or more halogen, or C$_{1-6}$ alkyl optionally substituted by one or more halogen), N(C$_{1-6}$ alkyl), or NCH$_2$(C$_{3-5}$ cycloalkyl).

12. A compound or salt according to claim 1 wherein Ar$^1$ is phenyl optionally substituted by one or two chlorine atoms.

13. A compound or salt according to claim 1 wherein X$^1$ is C$_{1-6}$ alkyl substituted by C$_{3-7}$ cycloalkyl, or is phenyl optionally substituted by one or more substituents independently selected from halogen and C$_{1-3}$ alkyl optionally substituted by one or more halogen.

14. A compound or salt according to claim 1 wherein R is SO$_2$Ph, SO$_2$CH$_3$,

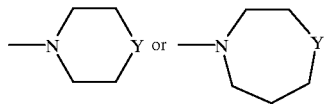

where Y is O, NCOCH$_3$, NCO$_2$C(CH$_3$)$_3$, NSO$_2$CH$_3$, NSO$_2$C$_2$H$_5$, NSO$_2$Ph, NSO$_2$CH$_2$Ph, NSO$_2$CH(CH$_3$)$_2$, NSO$_2$CH$_2$CF$_3$, NCOPh, CHF, NH, NCH$_2$Ph, or N-cyclopropylmethyl.

15. A compound or salt according to claim 1 wherein Ar$^1$ is phenyl, 4-chlorophenyl or 3,4-dichlorophenyl.

16. A compound or salt according to claim 1 wherein X$^1$ is (C$_{3-7}$ cycloalkyl)methyl, or phenyl optionally substituted by one or more substituents independently selected from halogen and methyl optionally substituted by one or more halogen.

17. A compound or salt according to claim 1 wherein R is SO$_2$Ph, SO$_2$CH$_3$,

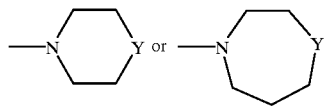

where Y is O, NCOCH$_3$, NCO$_2$C(CH$_3$)$_3$, NSO$_2$CH$_3$, NSO$_2$C$_2$H$_5$, NSO$_2$Ph, NSO$_2$CH$_2$Ph, NSO$_2$CH(CH$_3$)$_2$, NSO$_2$CH$_2$CF$_3$, NCOPh, or CHF.

18. A compound or salt according to claim 1 wherein X$^1$ is cyclopropylmethyl or phenyl optionally substituted by one or more fluorine or chlorine atoms.

19. A compound or salt according to claim 1 wherein X$^1$ is cyclopropylmethyl, phenyl, 3-chlorophenyl or 3,4-difluorophenyl.

20. A compound or salt according to claim 1 which is selected from:
(+)-3(R)-1-benzoyl-3-(3-[3-(4-tert-butoxycarbonylpiperazin-1-yl)azetidin-1-yl]propyl)-3-(3,4-dichlorophenyl)piperidine;
3(R)-1-benzoyl 3-(3-[3-(4-tert-butoxycarbonylhomopiperazin-1-yl)azetidin-1-yl]propyl)-3-(3,4-dichlorophenyl)piperidine;
(+)-3(R)-1-benzoyl-3-(3,4-dichlorophenyl)-3-(3-[3-(4-methanesulphonylpiperazin-1-yl)azetidin-1-yl]propyl) piperidine;
(+)-3(R)-3-(3-[3-(4-acetylpiperazin-1-yl)azetidin-1-yl] propyl)-1-benzoyl-3-(3,4-dichlorophenyl)piperidine;
(+)-3(R)-1-benzoyl-3-(3-[3-(4-benzoylpiperazin-1-yl) azetidin-1-yl]propyl)-3-(3,4-dichlorophenyl) piperidine;
(+)-3(R)-1-benzoyl-3-(3,4-dichlorophenyl)-3-(3-[3-(4-methanesulphonylpiperazin-1-yl)azetidin-1-yl]propyl) piperidine;
(+)-3(R)-3-(3-[3-(4-benzenesulphonylpiperazin-1-yl) azetidin-1-yl]propyl)-1-benzoyl-3-(3,4-dichlorophenyl)piperidine;
(+)-3(R)-1-benzoyl-3-(3-[3-(4-benzylsulphonylpiperazin-1-yl)azetidin-1-yl]propyl)-3-(3,4-dichlorophenyl)piperidine;
(+)-3(R)-1-benzoyl-3-(3,4-dichlorophenyl)-3-(3-[3-(4-iso-propylsulphonylpiperazin-1-yl)azetidin-1-yl] propyl)piperidine;
(+)-3(R)-1-benzoyl-3-(3,4-dichlorophenyl)-3-(3-[3-(4-(2,2,2-trifluoroethane)sulphonylpiperazin-1-yl)azetidin-1-yl]propyl)piperidine;

(+)-3(R)-1-benzoyl-3-(3,4-dichlorophenyl)-3-(3-[3-morpholinoazetidin-1-yl]propyl)piperidine;

(+)-3(R)-1-benzoyl-3-(3,4-dichlorophenyl)3-(3-[3-(N-methyl benzenesulphonamido)azetidin-1-yl]propyl) piperidine;

(+)-3(R)-1-benzoyl-3-(3,4-dichlorophenyl)-3-(3-[3-(N-phenyl methanesulphonamido)azetidin-1-yl]propyl) piperidine;

3(R)-1-benzoyl-3-(3,4-dichlorophenyl)3-(3-[3-(4-methanesulphonylhomopiperazin-1-yl)azetidin-1-yl] propyl)piperidine;

3(R)-1-benzenesulphonyl-3-(3,4-dichlorophenyl)3-(3-[3-(4-methanesulphonylpiperazin-1-yl)azetidin-1-yl] propyl)piperidine;

(+)-3(R)-1-(cyclopropylacetyl)-3-(3,4-dichlorophenyl 3-(3-[3-(4-methanesulphonylpiperazin-1-yl)azetidin-1-yl]propyl)piperidine;

(+)-3(R)-3-(3,4-dichlorophenyl)-1-(3,4-difluorobenzoyl)-3-(3-[3-(4-methanesulphonyl-piperazin-1-yl)azetidin-1-yl]propyl)piperidine;

(+)-3(R)-1-(3-chlorobenzoyl)-3-(3,4-dichlorophenyl)3-(3-[3-(4-methanesulphonylpiperazin-1-yl)azetidin-1-yl]propyl)piperidine;

(+)-3(R)-1-benzoyl-3-(3,4-dichlorophenyl)-3-(3-[3-piperazinoazetidin-1-yl]propyl)piperidine;

and 3(R)-1-benzoyl-3-(3,4-dichlorophenyl)-3-(3-[3-(homopiperazin-1-yl)azetidin-1-yl]propyl)piperidine;

and the pharmaceutically-acceptable salts thereof.

21. A pharmaceutical composition comprising a compound or salt according to claim 1 together with pharmaceutically acceptable diluent, adjuvant or carrier.

22. A method of treating a disease in a human or non-human animal which comprises administering to said human an effective amount of a compound or salt according to claim 1, where the disease is anxiety, depression, dyspepsia, irritable bowel syndrome, gastro-oesophageal reflux, faecal incontinence, colitis, ulcerative colitis, gastritis, gastroduodenal ulcers associated with *H. pylori* infection incontinence or cystitis.

* * * * *